(12) United States Patent  
Janssens et al.

(10) Patent No.: US 7,390,822 B2  
(45) Date of Patent: Jun. 24, 2008

(54) SUBSTITUTED 4-PHENYL-4-[1H-IMIDAZOL-2-YL]-PIPERIDINE DERIVATIVES FOR REDUCING ISCHAEMIC DAMAGE

(75) Inventors: Frans Eduard Janssens, Bonheiden (BE); Joseph Elisabeth Leenaerts, Rijkevorsel (BE); Francisco Javier Fernández-Gadea, Toledo (ES); Paul Joannes Ludovicus Herijgers, Kampenhout (BE); Theo Frans Meert, Boom (BE); Antonio Gómez-Sánchez, Toledo (ES); Willem Flameng, Oud-Heverlee (BE); Marcel J. M. Borgers, Oud-Turnhout (BE)

(73) Assignee: Janssen Pharmaceutica, N.V., Beerse (BE)

( * ) Notice: Subject to any disclaimer, the term of this patent is extended or adjusted under 35 U.S.C. 154(b) by 586 days.

(21) Appl. No.: 10/492,778

(22) PCT Filed: Oct. 10, 2002

(86) PCT No.: PCT/EP02/11371

§ 371 (c)(1),  
(2), (4) Date: Apr. 15, 2004

(87) PCT Pub. No.: WO03/039440

PCT Pub. Date: May 15, 2003

(65) Prior Publication Data

US 2005/0004170 A1 Jan. 6, 2005

(30) Foreign Application Priority Data

Oct. 15, 2001 (EP) ................................. 01203927

(51) Int. Cl.  
*A61K 31/445* (2006.01)  
*A61K 31/454* (2006.01)

(52) U.S. Cl. ........................ 514/326; 514/256; 544/333; 546/210

(58) Field of Classification Search ................. 514/256, 514/326; 544/333; 546/210  
See application file for complete search history.

(56) References Cited

FOREIGN PATENT DOCUMENTS

| GB | 2 332 373 A | 6/1999 |
|---|---|---|
| WO | WO 96/27380 A1 | 9/1996 |
| WO | WO 98/07832 A1 | 2/1998 |
| WO | WO 98/49300 A2 | 11/1998 |
| WO | WO 99/04795 A1 | 2/1999 |
| WO | WO 00/37470 A1 | 6/2000 |
| WO | WO 00/77008 A2 | 12/2000 |
| WO | WO 03/033466 A1 | 4/2003 |

OTHER PUBLICATIONS

Chien et al. "Method for employing . . . " CA 127:210338 (1997).*  
Buttner et al. "The neuropathology of heroin abuse" Forensic sci. int. v. 113, pp. 435-442 (2000).*  
Vanderklish et al. "The pathogenic activation of calpain . . . " J. Exp. Path. v.81, pp. 323-339 (2000).*  
Govindaswami et al., "Proceedings of the 11th International Hibernation Symposium 2000", pp. 377-384, Springer-Verlag, Berlin, Germany.  
Stella, V.J. et al., "Prodrugs: the control of drug delivery via bioreversible chemical modification," Drug Delivery Systems, 1980, pp. 112-176.  
Stella, V.J. et al., "Prodrugs: Do they Have Advantages in Clinical Practice?," Drugs 29, 1985, pp. 455-473.  
Malatynska E., et al., "Human δopioid Receptor: A stable cell line for functional studies of opioids", NeuroReport 6, 613-616, 1995.  
Portoghese, P.S., et al., "Naltrindole, a highly selective and potent non-peptide δopioid receptor antagonist", Eur. J. Pharmacol. 146, 185-186, 1988.  
ALT, A. et al., "Stimulation of guanosine-5'-O'(3[$^{35}$S]thio)triphosphate binding by endogenous opioids acting at a cloned Mu receptor", J. Pharmacol. Exp. Ther. 286, 282-288, 1988.

(Continued)

*Primary Examiner*—Celia Chang  
(74) *Attorney, Agent, or Firm*—Woodcock Washburn LLP

(57) ABSTRACT

The present invention relates to an agent for reducing ischaemic damage to an organ, in particular to a heart and a brain, pharmaceutical compositions comprising said agent and the use of said agent for the treatment of ischaemic diseases to the heart and the brain. The agent comprises a substituted 4-phenyl-4-[1H-imidazol-2-yl]-piperidine derivative according to Formula (I)

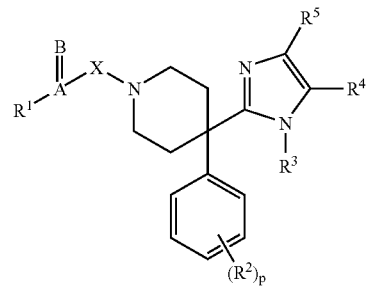

the pharmaceutically acceptable acid or base addition salts thereof, the stereochemically isomeric forms thereof, the tautomeric forms thereof, the N-oxide forms thereof and the prodrugs thereof. In particular are claimed the compounds according to Formula (I) in which A=B is C=O or $SO_2$, X is a covalent bond, $R^1$ is alkyloxy, alkyloxyalkyl, Ar or $NR^9R^{10}$, wherein $R^9$ and $R^{10}$ each independently are hydrogen or Ar; or A=B and $R^1$ together form a benzoxazolyl radical; p is zero, $R^3$ is benzyl optionally substituted with hydroxy, alkyl or alkyloxycarbonyl and $R^4$ and $R^5$ each are hydrogen. The use of said agents has important clinical ramifications with regard to the reduction of ischaemic damage to an organ in a mammal, in particular to a heart and/or a brain, the prevention of coronary artery diseases in a mammal by inducing a cardio-protective effect and the treatment and prevention of stroke.

16 Claims, 5 Drawing Sheets

OTHER PUBLICATIONS

Smart, D., et al., "The effects of recombinant rat μ-opioid receptor activation in CHO cells on phospholipase C, $[Ca^{2+}]l$ and adenylyl cyclase", Br. J. Pharmacol. 120, 1165-1171, 1997.

Bradford, M.M., "A rapid and sensitive method for the quantification of microgram quantities of protein utilizing the principle of protein-dye binding", Analytical Biochem, 72: 248-254, 1976.

Lazareno, S., "Measurement of agonist-stimulated $[^{35}S]GTP\gamma S$ binding to cell membranes" Meth. Molec. Biol. 106, 231-243, 1999.

Su T-P et al., "Novel Actions of a Delta Opioid Peptide Dadle: From Hibernation to Organ Preservation," Society for Neuroscience Abstracts, Society for Neuroscience, U.S., vol. 19, No. 1/3, 1993, pp. 421.

* cited by examiner

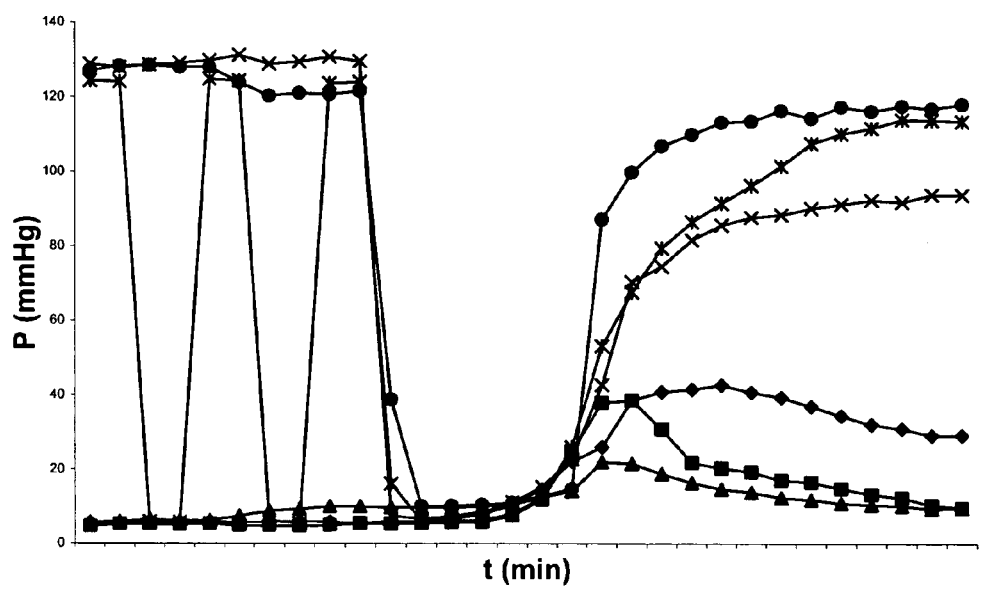
Figure 1 : End diastolic pressure (EDP) and Peak systolic pressure (PSP) for the 3 groups. --◆-- : EDP of Control group ; --■-- : EDP of Ischaemic preconditioned group; --▲-- : EDP of group treated with Compound 1 ; --✖-- : PSP of Control group ; -- ✳ -- : PSP of Ischaemic preconditioned group ; --●-- : PSP of group treated with Compound 1

Figure 2 : dP/dt$_{max}$ in the three groups. --♦-- : Control group ; --■-- : Ischaemic preconditioned group; --▲-- : Group treated with Compound 1
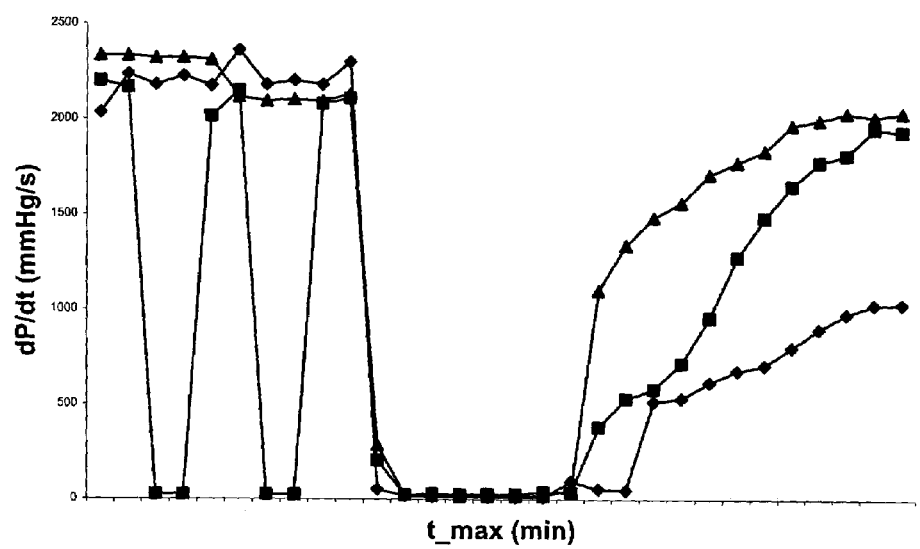

Figure 3 : Pressure-volume relationships in the left ventricle for the 3 groups. The studied parameter is the preload recruitable stroke work ($M_{SW}$).
A : Control Group ; B : Ischaemic preconditioned group ; C : Group treated with Compound 1.
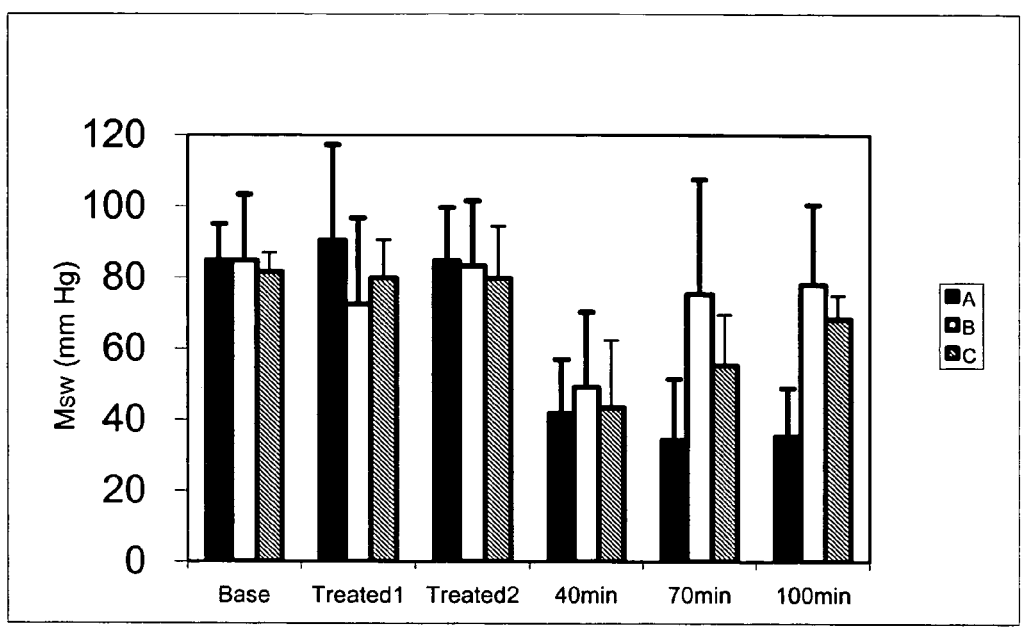

Figure 4: Ventricular relaxation for the 3 groups. The studied parameter is Tau.
A : Control Group ; B : Ischaemic preconditioned group ; C : Group treated with Compound 1.
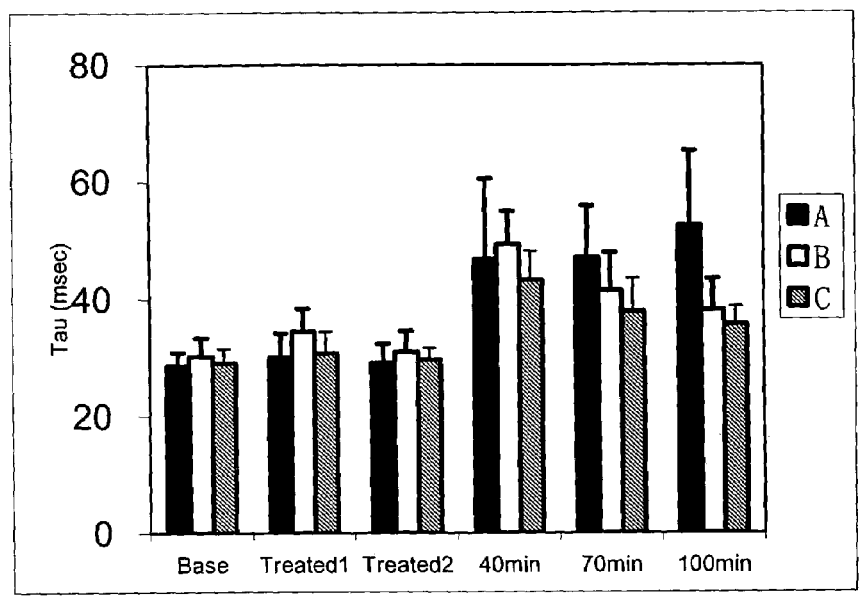

Figure 5 : SW/PVA for the 3 groups. A : Control Group ; B : Ischaemic preconditioned group ; C : Group treated with Compound 1.
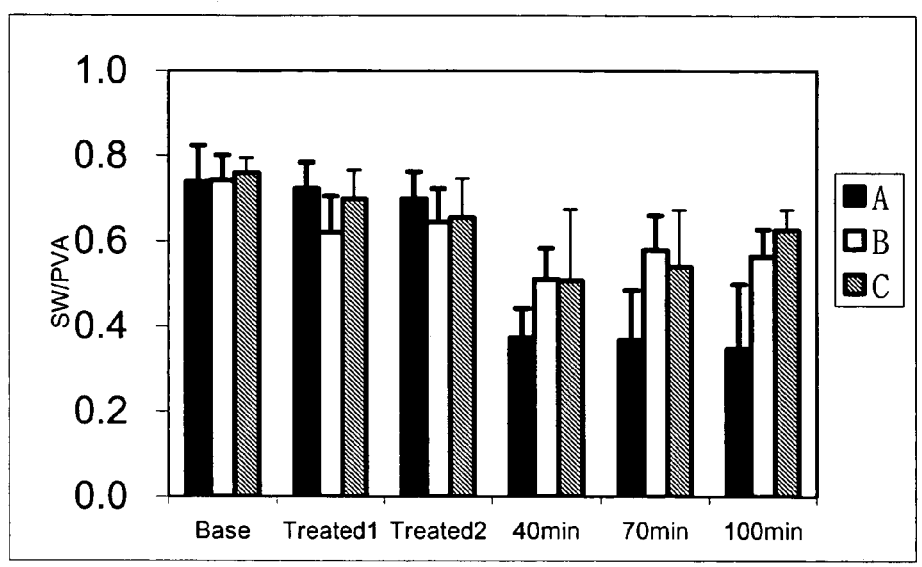

SUBSTITUTED 4-PHENYL-4-[1H-IMIDAZOL-2-YL]-PIPERIDINE DERIVATIVES FOR REDUCING ISCHAEMIC DAMAGE

CROSS REFERENCE TO RELATED APPLICATIONS

This application is the national stage of Application No. PCT/EP02/11371, filed Oct. 10, 2002, which application claims priority from EP 01203927.7 filed Oct. 15, 2001.

FIELD OF THE INVENTION

The present invention relates to 4-phenyl-4-[1H-imidazol-2-yl]-piperidine derivatives for reducing ischaemic damage to an organ, as well as to pharmaceutical compositions comprising said piperidine derivatives and the use of said piperidine derivatives for the prevention and treatment of ischaemic damage to an organ, in particular to reduce cardiac and cerebral ischaemic damage.

BACKGROUND OF THE INVENTION

In the framework of this application, ischaemia is defined as the reduction or loss of blood flow to a tissue, and associated therewith, the reduction or loss of e.g. oxygen suppletion to a tissue.

In the framework of this application, ischaemic damage is defined as the adverse effects associated with an ischaemic event, such as ischaemic necrosis or infarction. The metabolic events thought to underlie such cell degeneration and cell death comprise: energy failure through ATP depletion; cellular acidosis; glutamate release; calcium ion influx; stimulation of membrane phospholipid degradation and subsequent free-fatty-acid accumulation; and free radical generation.

There is a growing need for compounds that may provide protection against ischaemia and its associated adverse effects.

It has been found recently that certain highly specific delta-2 opioid receptor agonists can provide extended pharmacological induced ischaemic protection to the myocardium by a process similar to that which occurs in ischaemic preconditioning (IPC) (Govindaswami et al., in *Proceedings of the 11th International Hibernation Symposium* 2000, pp. 377-384, Springer-Verlag, Berlin, Germany). Ischaemic preconditioning describes the phenomenon that a short period of ischaemia preconditions the heart such that a subsequent period of ischaemia causes less damage. In turn, this results in a smaller myocardial infarction and fewer arrhythmias. The mechanism is thought to be based on modifications in the function (opening) of the mitochondrial ATP-sensitive K-channel (mitoK$_{ATP}$). One known delta-2 agonist is DADLE (D-Ala2-D-Leu5-enkephalin) which has been shown to induce the same effect as ischaemic preconditioning on an organ. Therefore, the mode of action of both ischaemic preconditioning and chemical compounds must be seen as a trigger to activate a more basal or protective cellular mode. Since delta opioid receptors are found in most tissues, including heart and brain tissue, it may be expected that the compounds exerting an ischaemic protection to e.g. heart tissue, will do the same to brain tissue, and also for example, to lung, kidney of liver tissue.

At present, there are two main therapeutic areas where ischaemia plays a important role: cardiac ischaemia and cerebral ischaemia or stroke.

Cardiac Ischaemia

Cardiac surgery is always associated with controlled imposition of one or more episodes of ischaemia and reperfusion. In conventional cardiac surgery, the heart is stopped and cooled with a cardioplegic solution to reduce myocardial oxygen consumption such that it is possible to impose a longer period of ischaemia on the heart without too much damage. However, this requires maintenance of the blood circulation by a system of extra corporal circulation, which has several important drawbacks: it induces a significant inflammatory body reaction, it causes micro-embolisms and it thoroughly disturbs the coagulation and fibrinolytic system of the blood. Moreover, the micro-embolisms and non-pulsatile circulation during surgery with extra corporal circulation are responsible for suboptimal perfusion of vital organs such as the brain, kidneys and intestines. This results e.g. in an increased anaerobic metabolism (increased lactate in the postoperative period), impaired kidney function and confusion.

Owing to the development of local (mechanical) stabilizers, over the past several years, in order to avoid the aforementioned drawbacks, coronary surgery has been performed without the aid of extra corporal circulation. The disadvantage however is that the heart remains normothermic and has to perform mechanical work while regional ischaemia is imposed. At present, worldwide over 30% of coronary surgery is performed without the use of extra corporal circulation. For this application a cardioprotective agent would be extremely useful. Such an agent should be able to exert a protective action on the myocardial tissue using a basal cellular mechanism, thereby prolonging the period of imposed ischaemia.

In addition, there is a potential field of application in donor heart preservation, which is still a current problem, since the acceptable period of ischaemia is still limited to 4 to 6 hours. Also, cardiac surgery requiring complex reconstructions with long periods of intra-operative cardiac ischaemia can benefit from a cardioprotective agent in addition to the presently used cardioplegic arrest.

In general, there is a potential field of application in all surgical and percutaneous interventional procedures where the ischaemia-reperfusion sequence imposed upon any organ plays a role, such as, for example, transplant surgery, aneurysm surgery, vascular surgery for obstructive vascular disease and percutaneous interventions on stenosed coronary, carotic and peripheral arteries.

Particularly, there is a potential field of application for patients before undergoing anesthesia for any reason, in which conditions of reduced blood supply to organs apply, such as, for example in stable and unstable angina, or conditions that can be caused by the hemodynamic effects of anesthesia, such as loss of blood pressure, as well as for patients during the first hours from the onset of a hart attack before the definitive formation of blood cloths.

Cerebral Ischaemia

The brain, more than any other organ in the body, depends, for its survival and proper functioning, on a relatively constant supply of oxygenated blood. While comprising only 2% of the body's weight, the brain receives 15% of the heart's output of blood and consumes 20% of the oxygen used by the body. In addition, a constant supply of blood is required to provide the brain with glucose, the major energy substrate used by the brain to produce high energy phosphates such as ATP (see for instance WO 96/27380 (Interneuron Pharmaceuticals, Inc.)).

In the framework of this application, cerebral ischaemia is defined as the interruption or reduction of blood flow in the arteries feeding the brain, usually as a result of a blood cloth (thrombus) or other matter (embolus) occluding the arteries, resulting into an ischaemic stroke. As defined herein, ischaemic stroke is a syndrome, caused by a diverse etiologies, such as atherosclerotic cerebrovascular disease such as for example hypoperfusion and arteriogenic emboli; penetrating artery disease; cardiogenic embolism, such as, but not limited to, atrial fibrillation, valve disease and ventricular thrombi; cryptogenic stroke; and other more unusual causes, such as, for example prothrombic states, dissections, arteritis, migraine or vasospasm and drug abuse (see for instance *Cardiovascular Thrombosis: Thrombocardiology and Thromboneurology*, edited by M. Verstraete, V. Fuster and E. J. Topol, Second Edition, Lippincot-Raven Publishers, Philadelphia, 1998).

Stroke is the third cause of death in the US, and about 500,000 new cases occur every year. Worldwide, stroke is the number one cause of death due to the particularly high incidence of stroke in Asia. Ischaemic stroke is the most common form of stroke and is responsible for about 85% of all strokes.

There is a potential field of application in the case of stroke prevention in certain cases, e.g. during surgery where there exists a risk for an ischaemic event, in the reduction of ischaemic damage in case of a stroke, in reducing the extent of cerebral infarction subsequent to cerebral ischaemia and in the treatment of ischaemic stroke, in particular the acute treatment of stroke after an ischaemic event.

BACKGROUND PRIOR ART

WO 99/04795 (Toray Industries Inc.) discloses certain tetracyclic pyridine and pyrazine derivatives having the pharmacological prophile of a delta opioid receptor agonist and their use for reducing ischaemic damage to an organ. The therein disclosed compounds are not structurally related to the compounds of the present invention.

WO 00/37470 (Janssen Pharmaceutica N.V.) discloses a number of 4-phenyl-4-[1h-imidazol-2-yl]-piperidine derivatives, however not forming part of the scope of this invention and used as intermediates for the synthesis of antihistaminic compounds.

SUMMARY OF THE INVENTION

In this application, a novel group of compounds is described, based on a substituted 4-phenyl-4-[1H-imidazol-2-yl]-piperidine derivative, that has important clinical ramifications with regard to the reduction of ischaemic damage to an organ in a mamal, in particular to heart and brain tissue, in particular for the prevention of complications and consequences of coronary artery diseases in a mamal by inducing a cardioprotective effect.

The object of the present invention is an agent for reducing ischaemic damage to an organ in a mammal, which comprises as effective ingredient a substituted 4-phenyl-4-[1H-imidazol-2-yl]-piperidine derivative according to the general Formula (I)

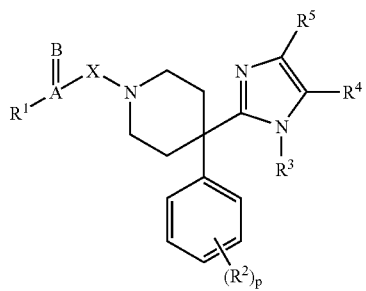

the pharmaceutically acceptable acid or base addition salts thereof, the stereochemically isomeric forms thereof, the tautomeric forms thereof and the N-oxide forms thereof, wherein:

A=B is bivalent π-bond radical;π

X is a covalent bond, —CH$_2$— or CH$_2$CH$_2$—;

R$^1$ is hydrogen, alkyloxy, alkylcarbonyloxy, Ar-oxy, Het-oxy, Ar-carbonyloxy, Het-carbonyloxy, Ar-alkyloxy, Het-alkyloxy, alkyl, polyhaloalkyl, alkyloxyalkyl, Ar-alkyl, Het-alkyl, Ar, Het, thio, alkylthio, Ar-thio, Het-thio or NR$^9$R$^{10}$ wherein R$^9$ and R$^{10}$ each independently are hydrogen, alkyl, Ar, Ar-alkyl, Het, Het-alkyl, Ar-carbonyl, Het-carbonyl or alkyloxycarbonylalkyl; or A=B and R$^1$ together form an optionally substituted semi-aromatic or aromatic carbocyclic or heterocyclic radical Het$^2$ or Het$^3$;

R$^2$ is hydroxy, alkyloxy, alkylcarbonyloxy, phenyloxy, phenylcarbonyloxy, halo, cyano, alkyl, polyhaloalkyl, alkyloxyalkyl, formyl, carboxy, alkylcarbonyl, alkyloxycarbonyl, aminocarbonyl, mono- or dialkylaminocarbonyl, phenyl, nitro, amino, mono- or dialkyl-amino, thio or alkylthio;

R$^3$ is alkyl, Ar, Ar-alkyl, Ar-alkenyl, Ar-carbonyl, Het, Het-alkyl, Het-alkenyl or Het-carbonyl;

R$^4$, R$^5$ each independently is hydrogen, alkyl, carboxy, aminocarbonyl, alkyloxycarbonyl, halo or hydroxyalkyl;

p is an integer equal to zero, 1, 2 or 3;

BRIEF DESCRIPTION OF DRAWNING

FIG. 1: End diastolic pressure (EDP) and Peak systolic pressure (PSP) for the 3 groups. —♦—: EDP of Control group —■—: EDP of Ischaemic preconditioned group; —▲—: EDP of group treated with Compound 1; —×—: PSP of Control group ; —*—: PSP of lschaemic preconditioned group —●—: PSP of group treated with Compound 1.

FIG. 2: dP/dt$_{max}$ in the three groups. —♦—: Control group; —■—: lschaemic preconditioned group; —▲—: Group treated with Compound 1.

FIG. 3: Pressure-volume relationships in the left ventricle for the 3 groups. The studied parameter is the preload recruitable stroke work(M$_{sw}$). A: Control Group; B: Tschaemic preconditioned group C: Group treated with Compound 1.

FIG. 4: Ventricular relaxation for the 3 groups. The studied pammeter is Tau. A: Control Group; B: Isebsemic preconditioned group; .C: Group treated with Compound 1.

FIG. 5: SWIPVA for the 3 groups. A: Control Group; B: Ischaemic preconditioned group; C: Group treated with Compound 1.

DETAILED DESCRIPTION OF THE INVENTION

In the framework of this application, alkyl is a straight or branched saturated hydrocarbon radical having from 1 to 6 carbon atoms; or is a cyclic saturated hydrocarbon (cycloalkyl) radical having from 3 to 7 carbon atoms; or is a cyclic saturated hydrocarbon radical having from 3 to 7 carbon atoms attached to a straight or branched saturated hydrocarbon radical having from 1 to 6 carbon atoms; wherein each carbon atom may be optionally substituted with amino, nitro, thio, hydroxy, oxo, cyano, formyl or carboxy. Preferably, alkyl is methyl, ethyl, propyl, isopropyl, butyl, tert-butyl, cyclopropyl, cyclopentyl, cyclohexyl, cyclohexylmethyl and cyclohexylethyl.

In the framework of this application, alkenyl is an alkyl radical as defined above having one or more double bonds. Preferably, alkenyl is ethenyl and propenyl.

In the framework of this application, Ar is a homocycle selected from the group of phenyl and naphthyl, each optionally substituted with one or more substituents, each substituent independently selected from the group of hydroxy, alkyloxy, alkylcarbonyloxy, phenyloxy, phenylcarbonyloxy, halo, cyano, alkyl, polyhaloalkyl, alkyloxyalkyl, formyl, haloformyl, carboxy, alkylcarbonyl, alkyloxycarbonyl, aminocarbonyl, mono- or dialkylaminocarbonyl, phenylalkyl, phenyl, nitro, amino, mono- or dialkyl-amino, thio, alkylthio or $SO_2$—$CH_3$. Preferably, Ar is naphthyl or phenyl, each optionally substituted with hydroxy, methyloxy, ethyloxy, phenyloxy, trihalomethyloxy, halo, methyl, trifluoromethyl, chloroformyl, carboxy, methyloxycarbonyl, ethyloxycarbonyl, diethylaminocarbonyl, phenyl, nitro, methylthio, trifluoromethyloxy or $SO_2$-$C_{1-3}$alkyl.

In the framework of this application, halo is a substituent selected from the group of fluoro, chloro, bromo and iodo and polyhaloalkyl is a straight or branched saturated hydrocarbon radical having from 1 to 6 carbon atoms or a cyclic saturated hydrocarbon radical having from 3 to 7 carbon atoms, wherein one or more carbon atoms is substituted with one or more halo-atoms. Preferably, halo is bromo, fluoro or chloro and preferably, polyhaloalkyl is trifluoromethyl.

In the framework of this application, Het is a heterocyclic radical selected from the group of $Het^1$, $Het^2$ and $Het^3$. $Het^1$ is an aliphatic monocyclic heterocyclic radical selected from the group of pyrrolidinyl, dioxolyl, imidazolidinyl, pyrrazolidinyl, piperidinyl, dioxyl, morpholinyl, dithianyl, thiomorpholinyl, piperazinyl and tetrahydrofuranyl. $Het^2$ is a semi-aromatic monocyclic heterocyclic radical selected from the group of 2H-pyrrolyl, pyrrolinyl, imidazolinyl and pyrrazolinyl. $Het^3$ is an aromatic monocyclic heterocyclic radical selected from the group of pyrrolyl, pyrazolyl, imidazolyl, furanyl, thienyl, oxazolyl, isoxazolyl, thiazolyl, isothiazolyl, pyridinyl, pyrimidinyl, pyrazinyl, pyridazinyl or triazinyl; or an aromatic bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocyclic radical may optionally be substituted on a carbon atom and/or an heteroatom with halo, hydroxy, alkyloxy, alkyl, Ar, Ar-alkyl or pyridinyl.

An interesting group of compounds are those compounds according to Formula (I), the pharmaceutically acceptable acid or base addition salts thereof, the stereochemically isomeric forms thereof, the tautomeric forms thereof and the N-oxide forms thereof, in which A=B is selected from the group of C=O, C=N—$R^6$ wherein $R^6$ is hydrogen or cyano, C=S, S=O, $SO_2$ and C=$CR^7R^8$ wherein $R^7$ and $R^8$ each independently are hydrogen, nitro or alkyl.

Another interesting group of compounds are those compounds according to Formula (I), the pharmaceutically acceptable acid or base addition salts thereof, the stereochemically isomeric forms thereof, the tautomeric forms thereof and the N-oxide forms thereof, in which $R^1$ is selected from the group of alkyloxy, Ar-alkyloxy, alkyl, polyhaloalkyl, alkyloxyalkyl, Ar-alkyl, Het-alkyl, Ar, piperazinyl, pyrrolyl, thiazolyl, pyrrolidinyl and $NR^9R^{10}$ wherein $R^9$ and $R^{10}$ each independently are hydrogen, alkyl, Ar, Ar-alkyl, pyridinyl or alkyloxycarbonylalkyl.

Another interesting group of compounds are those compounds according to Formula (I), the pharmaceutically acceptable acid or base addition salts thereof, the stereochemically isomeric forms thereof, the tautomeric forms thereof and the N-oxide forms thereof, in which A=B and $R^1$ together form a radical selected from the group of $Het^2$ and $Het^3$. More preferably, A=B and $R^1$ together form a radical selected from the group of benzoxazolyl, thiazolyl, benzothiazolyl, benzimidazolyl and pyrimidinyl.

Yet another interesting group of compounds are those compounds according to Formula (I), the pharmaceutically acceptable acid or base addition salts thereof, the stereochemically isomeric forms thereof, the tautomeric forms thereof and the N-oxide forms thereof, in which X is a covalent bond or a —$CH_2$-moiety. Preferably, X is a covalent bond.

Yet another interesting group of compounds are those compounds according to Formula (I), the pharmaceutically acceptable acid or base addition salts thereof, the stereochemically isomeric forms thereof, the tautomeric forms thereof and the N-oxide forms thereof, in which $R^2$ is alkyloxy or halo.

Yet another interesting group of compounds are those compounds according to Formula (I), the pharmaceutically acceptable acid or base addition salts thereof, the stereochemically isomeric forms thereof, the tautomeric forms thereof and the N-oxide forms thereof, in which $R^3$ is selected from the group of phenylalkyl and naphthyl, each independently substituted with at least one substituent selected from the group of halo, alkyloxycarbonyl, hydroxy, alkyloxy and dialkylaminocarbonyl.

When $R^3$ is alkyl, then preferentially, alkyl is cyclohexylmethyl.

Still another interesting group of compounds are those compounds according to Formula (I), the pharmaceutically acceptable acid or base addition salts thereof, the stereochemically isomeric forms thereof, the tautomeric forms thereof and the N-oxide forms thereof, in which A=B is C=O or $SO_2$, $R^1$ is alkyloxy, alkyloxyalkyl, Ar or $NR^9R^{10}$, wherein $R^9$ and $R^{10}$ each independently are hydrogen or Ar; or A=B and $R^1$ together form a benzoxazolyl radical; p is zero, $R^3$ is benzyl optionally substituted with hydroxy, alkyl or alkyloxycarbonyl and $R^4$ and $R^5$ each are hydrogen.

More specifically, the following compounds are the most preferred compounds:

1-ethoxycarbonyl-4-phenyl-4-[1-(phenylmethyl)-1H-imidazol-2-yl]-piperidine;
1-propyloxycarbonyl-4-phenyl-4-[1-(phenylmethyl)-1H-imidazol-2-yl]-piperidine;
1-ethoxycarbonyl-4-phenyl-4-[1-[(4-hydroxyphenyl)methyl]-1H-imidazol-2-yl]-piperidine;
1-ethoxycarbonyl-4-phenyl-4-[1-(1-phenylethyl)-1H-imidazol-2-yl]-piperidine;
1-isopropyloxycarbonyl-4-phenyl-4-[1-(phenylmethyl)-1H-imidazol-2-yl]-piperidine;
1-ethoxycarbonyl-4-phenyl-4-[1-[[4-(methoxycarbonyl)phenyl]methyl]-1H-imidazol-2-yl]-piperidine;
1-benzoyl-4-phenyl-4-[1-(phenylmethyl)-1H-imidazol-2-yl]-piperidine;
1-(methoxyacetyl)-4-phenyl-4-[1-(1-phenylethyl)-1H-imidazol-2-yl]-piperidine;
4-[[2-(1-benzoyl-4-phenyl-4-piperidinyl)-1H-imidazol-1-yl]methyl]-methylbenzoate;

4-[[2-[1-(2-benzoxazolyl)-4-phenyl-4-piperidinyl]-1H-imidazol-1-yl]methyl]-methylbenzoate;
1-benzoyl-4-phenyl-4-[1-(1-phenylethyl)-1H-imidazol-2-yl]-piperidine;
1-ethoxycarbonyl-4-phenyl-4-[1-[1-[4-(ethoxycarbonyl)phenyl]ethyl]-1H-imidazol-2-yl]-piperidine and
N,4-diphenyl-4-[1-(phenylmethyl)-1H-imidazol-2-yl]-1-piperidinesulfonamide.

The pharmaceutically acceptable acid addition salts are defined to comprise the therapeutically active non-toxic acid addition salt forms which the compounds according to Formula (I) are able to form. Said acid addition salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, mandelic acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to Formula (I) as well as the salts thereof, are able to form. Such solvates are, for example, hydrates and alcoholates.

The term "stereochemically isomeric forms" as used herein defines all possible isomeric forms which the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of Formula (I) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

We note that the substituted carbon atom in the 4-position in the piperidinyl moiety is an achiral atom; therefore, compounds of Formula (I) may only have at least one stereogenic center in their structure by virtue of a chiral substituent $R^1$, $R^2$, $R^3$, $R^4$ or $R^5$.

The tautomeric forms of the compounds of Formula (I) are meant to comprise those compounds of Formula (I) wherein e.g. an enol group is converted into a keto group (keto-enol tautomerism).

The N-oxide forms of the compounds according to Formula (I) are meant to comprise those compounds of Formula (I) wherein one or several nitrogen atoms are oxidized to the so-called N-oxide, particularly those N-oxides wherein the nitrogen of the piperidinyl moiety and/or the imidazolyl moiety is oxidized.

The compounds of Formula (I) as prepared in the processes described below may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a $C_{1-6}$alkyl, phenyl, benzyl or one of the following groups:

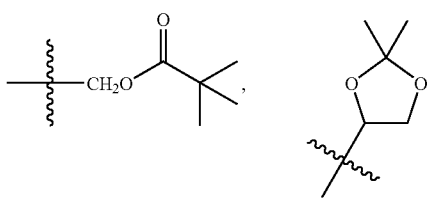

Amidated groups include groups of the formula —CONR$^y$R$^z$, wherein R$^y$ is H, $C_{1-6}$alkyl, phenyl or benzyl and R$^z$ is —OH, H, $C_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

Preferentially, the organ is a heart, a brain, a liver, a lung or a kidney and the mammal is a human.

More specifically, a preferred embodiment of the present invention relates to an agent for reducing ischaemic damage to the heart of a mammal, which comprises as effective ingredient a compound according to Formula (I), the pharmaceutically acceptable acid or base addition salts thereof, the stereochemically isomeric forms thereof, the tautomeric forms thereof and the N-oxide forms thereof. Preferentially, the mammal is a human.

The conditions relating to ischaemic damage to the heart are, for example, coronary ischaemic syndrome, angina pectoris, unstable angina pectoris, angina pectoris after myocardial infarction, myocardial infarction, acute myocardial infarction, cardioprotection in traditional cardiopulmonary bypass (CPB) surgery as well as off-bypass cardiac surgery, in non-cardiac surgery in humans with known or at risk of coronary artery disease (CAD) and coronary restenosis after PTCA. In the framework of this application, ischaemic damage shall be interpreted as any damage to any part of the heart, including the coronaries, and comprising direct cellular damage due to e.g. lack of oxygen as well as indirect damages.

More specifically, a preferred embodiment of the present invention relates to an agent for reducing ischaemic damage to a brain of a mammal, which comprises as effective ingredient a compound according to Formula (I), the pharmaceutically acceptable acid or base addition salts thereof, the stereochemically isomeric forms thereof, the tautomeric forms thereof and the N-oxide forms thereof. Preferentially, the mammal is a human.

The conditions relating to stroke are, for example, artherosclerotic cerebrovascular disease such as for example hypoperfusion and arteriogenic emboli; penetrating artery disease; cardiogenic embolism, such as, but not limited to, atrial fibrillation, valve disease and ventricular thrombi; cryptogenic stroke; and other more unusual causes, such as, for example prothrombic states, dissections, arteritis, migraine or vasospasm and drug abuse. Ischaemic damage is interpreted as any damage to any part of the brain, including direct cellular damage due to e.g. lack of oxygen and indirect damages, e.g. the increase of the intracranial pressure.

More specifically, a preferred embodiment of the present invention relates to an agent for inducing a cardioprotective effect in a mammal which comprises as effective ingredient a compound according to Formula (I), the pharmaceutically acceptable acid or base addition salts thereof, the stereochemically isomeric forms thereof, the tautomeric forms thereof, the N-oxide forms thereof and the prodrugs thereof. With cardioprotective effect is meant the effect that heart tissue is more protected against ischaemia than non-protected heart tissue.

In other preferred embodiments, the organ is a lung, a liver or a kidney.

The invention also relates to a pharmaceutical composition for reducing ischaemic damage to an organ in a mammal, comprising a pharmaceutically acceptable carrier and, as active ingredient, a therapeutically effective amount of a compound according to Formula (I), the pharmaceutically acceptable acid or base addition salts thereof, the stereochemically isomeric forms thereof, the tautomeric forms thereof, the N-oxide forms thereof and the prodrugs thereof.

Preferentially, the organ is a heart, a brain, a liver, a lung or a kidney and the mammal is a human.

More specifically, a preferred embodiment of the present invention relates to a pharmaceutical composition for reducing ischaemic damage to the heart in a mammal, a pharmaceutically acceptable carrier and, as active ingredient, a therapeutically effective amount of a compound according to Formula (I), the pharmaceutically acceptable acid or base addition salts thereof, the stereochemically isomeric forms thereof, the tautomeric forms thereof, the N-oxide forms thereof and the prodrugs thereof. Preferentially, the mammal is a human.

More specifically, a preferred embodiment of the present invention relates to a pharmaceutical composition for reducing ischaemic damage to a brain in a mammal, comprising a pharmaceutically acceptable carrier and, as active ingredient a compound according to Formula (I), the pharmaceutically acceptable acid or base addition salts thereof, the stereochemically isomeric forms thereof, the tautomeric forms thereof, the N-oxide forms thereof and the prodrugs thereof. Preferentially, the mammal is a human.

Another preferred embodiment of this invention relates to a pharmaceutical composition for inducing a cardioprotective effect in a mammal, comprising a pharmaceutically acceptable carrier and, as active ingredient a compound according to Formula (I), the pharmaceutically acceptable acid or base addition salts thereof, the stereochemically isomeric forms thereof, the tautomeric forms thereof, the N-oxide forms thereof and the prodrugs thereof. Preferentially, the mammal is a human.

Another preferred embodiment of this invention relates to a pharmaceutical composition in the form of a cardioplegic solution containing an effective amount of a compound according to Formula (I), the pharmaceutically acceptable acid or base addition salts thereof, the stereochemically isomeric forms thereof, the tautomeric forms thereof, the N-oxide forms thereof, the prodrugs thereof and a suitable carrier.

In another preferred embodiment, the compounds according to the invention may be administered in combination, either simultaneously or sequentially with an antithrombotic agent and/or an angiogenic growth factor. As antithrombotic agent could be chosen any agent known to exert such an effect, for example, but not limited to, a glycoprotein IIb/IXia antagonist, a thrombin inhibitor, a factor Xa inhibitor, a tissue factor pathway inhibitor, a thrombin receptor antagonist or a low molecular weight heparin. As angiogenic growth factor could be chosen a vascular endothelial growth factor (VEGF) such as the ones disclosed in GB-2332 373 A (Merck & Co, Inc.), which content is included in the current application by reference or for example as disclosed in WO 98/07832 (Ludwig Institute for Cancer research) or WO 98/49300 (Collateral Therapeutics). The above embodiment offers the advantage that the risk of acute coronary ischaemic syndrome is reduced in patients at risk of said syndrome. Patients at risk include those who suffer initial coronary ischaemic syndrome symptoms and who are therefore more likely than others who have not suffered such symptoms to experience further thrombosis and ischaemic tissue damage. Especially patients are envisaged who suffered a coronary infarct and are administered the pharmaceutical composition according to the above embodiment within 6 hours after the onset of the infarct and before the definitive blood cloth formation sets in. The above embodiment then provides the patient with a reduced likelihood of further cloth formation while reducing tissue damage and enhancing tissue repair. Also envisioned are patients under thrombolitic treatment for peripheral arterial occlusion or in general for treatment of thrombosis caused by the liberation of a thrombus and obstruction of a cranial blood vessel.

The invention therefore also relates to a pharmaceutical composition for the treatment of a mammal who has experienced an ischaemic event comprising an effective amount of a compound according to the invention and at least a second therapeutic agent, comprising an antithrombotic agent and/or an angiogenic growth factor, or their respective pharmaceutical acceptable acid or base addition salts thereof, the stereochemically isomeric forms thereof, the tautomeric forms thereof, the N-oxide forms thereof and the prodrugs thereof and a suitable carrier, as well as the use of a compound according to the invention for the preparation of a medicament for reducing cardiac ischaemic damage, comprising the a compound according to the invention and at least a second therapeutic agent, comprising an antithrombotic agent and/or an angiogenic growth factor.

Specifically, the compound according to Formula (I), the pharmaceutically acceptable acid or base addition salts thereof, the stereochemically isomeric forms thereof, the tautomeric forms thereof, the N-oxide forms thereof and the prodrugs thereof and the compositions thereof may also have high potential for donor organ preservation.

The agent for reducing ischaemic damage to an organ in a mammal according to the present invention may be administered per se. However, it may usually be administered in various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration by parenteral injection or infusion. For example, in preparing the compositions, any of the usual pharmaceutical media may be employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredient, and, from 1 to 99.95% by weight, more preferably from 30 to 99.9 weight % of a pharmaceutically acceptable carrier, all percentages being based on the total composition.

The dosages are appropriately selected depending on factors such as symptoms, age, body weight and methods of administration, but in case of parental administration such as injections for adults, 0.01 mg to 1.0 g of the compound according to the invention may be administered per day, either at once or spread over several administrations. In the case of oral administration for adults, 0.1 mg to 3 g of the compound according to the invention may be administered per day, either at once or spread over several administrations.

The pharmaceutical composition may additionally contain various other ingredients known in the art, for example, a stabilizing agent, buffering agent, emulsifying agent, viscosity-regulating agent, surfactant or preservative.

Preferably, the pharmaceutical composition is administered intravenously, for example by infusion (continuous intravenous administration) or bolus administration.

Further, the present invention also relates to the use of a compound of Formula (I), the pharmaceutically acceptable acid or base addition salts thereof, the stereochemically isomeric forms thereof, the tautomeric forms thereof, the N-oxide forms thereof and the prodrugs thereof, as well as any of the aforementioned pharmaceutical compositions thereof for the manufacture of a medicament for reducing ischaemic damage to an organ in a mammal.

Preferentially, the organ is a heart, a brain, a liver, a lung or a kidney and the mammal is a human.

More specifically, a preferred embodiment of the present invention relates to the use of a compound of Formula (I), the pharmaceutically acceptable acid or base addition salts thereof, the stereochemically isomeric forms thereof, the tautomeric forms thereof, the N-oxide forms thereof and the prodrugs thereof as well as any of the aforementioned pharmaceutical compositions thereof for the manufacture of a medicament for reducing ischaemic damage to a heart in a mammal, preferably a human.

More specifically, a preferred embodiment of the present invention relates to the use of a compound of Formula (I), the pharmaceutically acceptable acid or base addition salts thereof, the stereochemically isomeric forms thereof, the tautomeric forms thereof, the N-oxide forms thereof and the prodrugs thereof as well as any of the aforementioned pharmaceutical compositions thereof for the manufacture of a medicament for reducing ischaemic damage to a brain in a mammal, preferably a human.

Furthermore, the present invention also relates to the use of a compound of Formula (I), the pharmaceutically acceptable acid or base addition salts thereof, the stereochemically isomeric forms thereof, the tautomeric forms thereof, the N-oxide forms thereof and the prodrugs thereof as well as any of the aforementioned pharmaceutical compositions thereof for the manufacture of a medicament for inducing a cardioprotective effect in a mammal, preferably a human.

Furthermore, the present invention also relates to the use of a compound of Formula (I), the pharmaceutically acceptable acid or base addition salts thereof, the stereochemically isomeric forms thereof, the tautomeric forms thereof, the N-oxide forms thereof and the prodrugs thereof as well as any of the aforementioned pharmaceutical compositions thereof for the manufacture of a medicament for the treatment of a mammal who has experienced an ischaemic event comprising administering an effective amount of a compound according to the invention and at least a second therapeutic agent, comprising an antithrombotic agent and/or an angiogenic growth factor, or their respective pharmaceutical acceptable acid or base addition salts thereof, the stereochemically isomeric forms thereof, the tautomeric forms thereof, the N-oxide forms thereof and the prodrugs thereofand a suitable carrier.

The invention also relates to a method for reducing ischaemic damage to an organ, in particular a heart and/or a brain, in a mammal, in particular a human, or a method for inducing a cardioprotective effect in a mammal comprising the step of administering to said mammal in need of such a treatment a therapeutically effective amount of a compound according to Formula (I), the pharmaceutically acceptable acid or base addition salts thereof, the stereochemically isomeric forms thereof, the tautomeric forms thereof, the N-oxide forms thereof and the prodrugs thereof as well as any of the aforementioned pharmaceutical compositions thereof.

Further, the present invention also relates to the use of a compound of Formula (I), the pharmaceutically acceptable acid or base addition salts thereof, the stereochemically isomeric forms thereof, the tautomeric forms thereof, the N-oxide forms thereof and the prodrugs thereof as well as any of the aforementioned pharmaceutical compositions thereof for the manufacture of a medicament for the prevention and/or treatment of an cardiac or cerebral ischaemic event in a mammal The compounds according to the invention can generally be prepared by a succession of steps, each of which is known to the skilled person. In particular, the compounds according to Formula (I-a) can be prepared by reacting an intermediate of Formula (II) according to reaction scheme (1), a reaction that is performed in a suitable reaction-inert solvent, such as toluene, in the presence of a suitable base, such as triethylamine In reaction scheme (1), all variables are defined as in Formula (I) and $W^1$ together with the moiety it is attached to is equal to $R^1$; examples of $W^1$ are alkyl, Ar or Het. An example of $W^1OC(=O)Cl$ is chloroformiate.

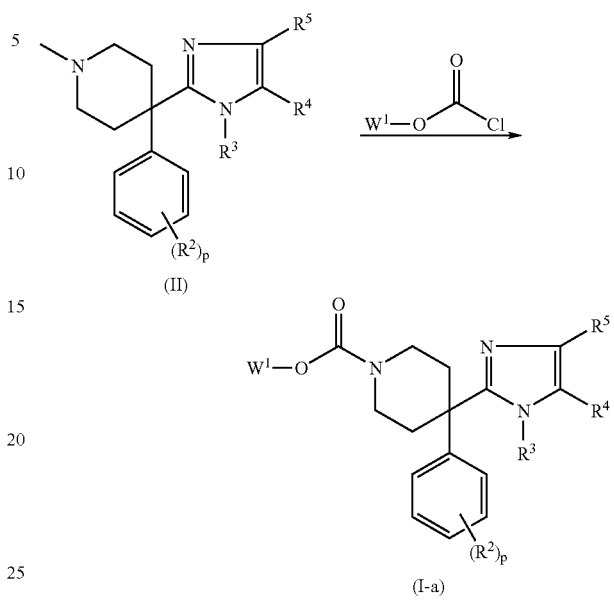

Scheme 1

The compounds according to Formulas (I-a), (I-b), (I-c), (I-d), (I-e), (I-f), (I-g) and (I-h) can also be prepared by reacting an intermediate of Formula (III) according to any of the reactions shown in reaction scheme (2). In said reactions, all variables are defined as in Formula (I) and $W^1$ together with the moiety it is attached to is equal to $R^1$; examples of $W^1$ are alkyl, Ar or Het.

Reaction (a) is performed in a suitable solvent such as dichloroethane and using $BOC_2O$. The reaction is conveniently carried out for several hours under reflux.

Reaction (b) is performed in a suitable solvent such as THF. The reaction is conveniently carried out for one to several hours at room temperature.

Reaction (c) is performed in a suitable solvent such as dichloromethane in the presence of a suitable base such as $Et_3N$ at room temperature for one hour.

Reaction (d) is performed in a suitable solvent such as THF or DMF at room temperature for several hours with no base needed.

Reaction (e) is performed either in refluxing acetone or in DMF in the presence of a suitable base such as potassium carbonate and can conveniently be carried out at 80° C.

Reaction (f) is performed in a suitable solvent such as dichloromethane in the presence of a suitable base such as triethylamine and at room temperature for about 30 to 120 minutes.

Reaction (g) is performed in a suitable solvent such as acetonitril under reflux for 24 hours.

Reaction (h) is performed under different conditions depending on $R^1$; for example when $R^1=CF_3$ the reaction is performed in the presence of triethylamine in dichloromethane at −78° C. for 1 hour. For $R^1=NH_2$, the reaction is conducted in dioxane for 12 hours at reflux temperature. For $R^1=CH_3$ the reaction is conducted in dichloromethane at room temperature for 3 hours in the presence of triethylamine.

Reaction (i) is performed in a suitable solvent such as isopropanol at reflux temperature for 12-36 hours.

Reaction (j) is performed in a suitable solvent such as acetonitril at reflux temperature for 24 hours.

Scheme 2
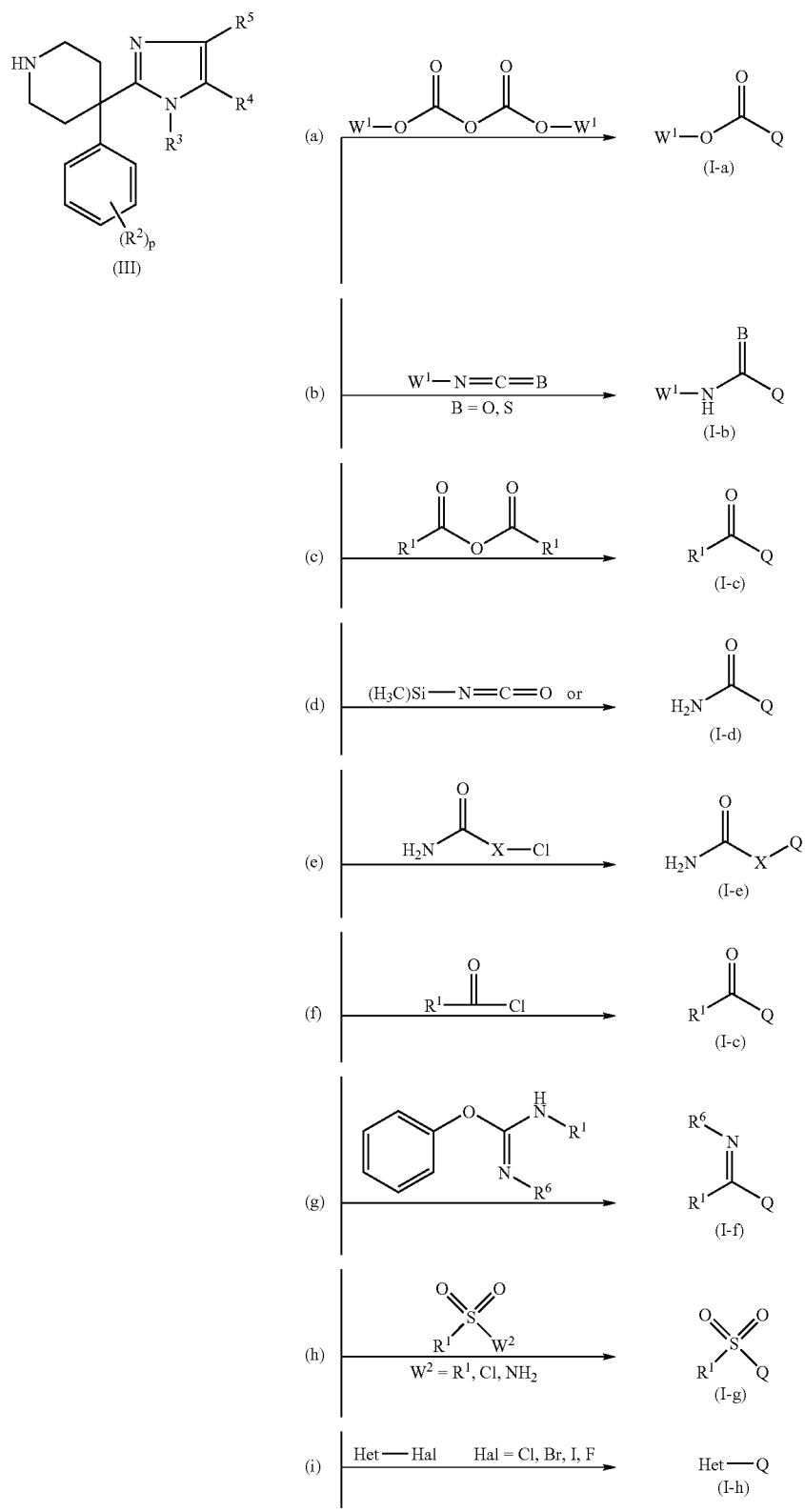

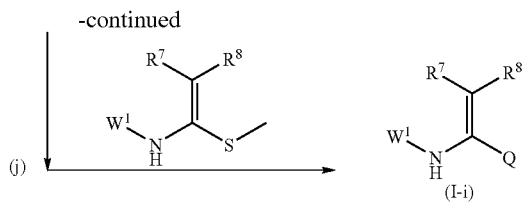

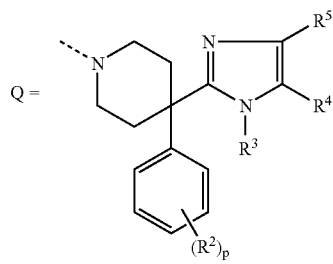

The compounds according to Formulas (I-c) can also be prepared by reacting an intermediate of Formula (IV) with an halide. In said reaction, all variables are defined as in Formula (I). The reaction is performed with a base such as NaH (60% in mineral oil) and in a reaction-inert solvent such as DMF or THF.

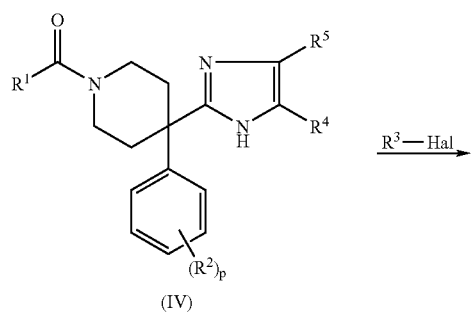

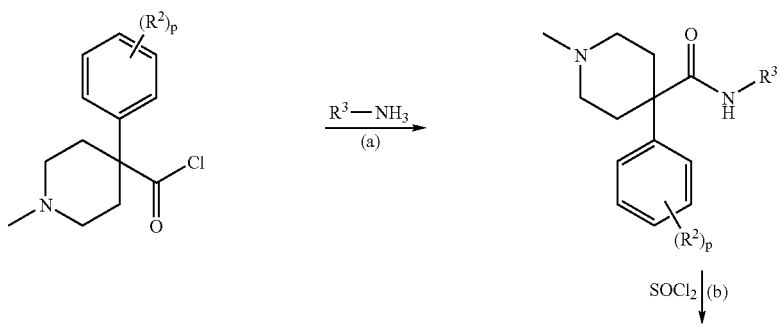

The starting material and the intermediate compounds according to Formulas (II), (III) and (IV) are compounds that are either commercially available or may be prepared according to conventional reaction procedures generally known in the art.

Intermediate compounds of Formula (II) may be prepared according to the following reaction scheme (4) wherein all variables are defined as in Formula (I):

Scheme 4

-continued

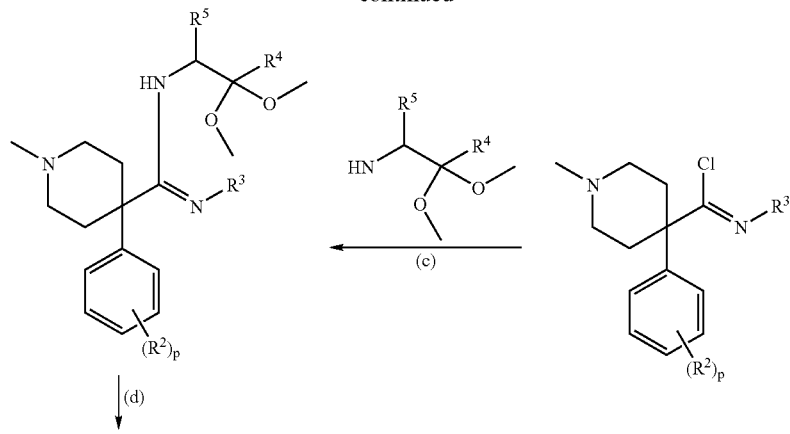

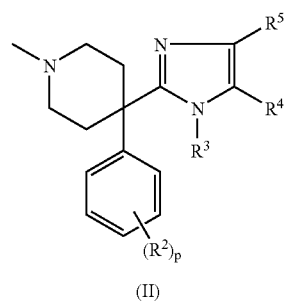

(II)

Reaction scheme 4 comprises the step (a) in which an acylchloride of the type shown is reacted with a substituted primary amine, e.g. benzylamine, in the presence of a suitable base, such as Et₃N and in a suitable reaction-inert solvent, such as dichloromethane. The reaction may conveniently carried out at room temperature. In a next step (b), the adduct obtained in step (a) is refluxed with SOCl₂, after which the product obtained is reacted with appropriately substituted 2,2-dimethoxyethylamine in a reaction-inert solvent, such as DMF, for instance at room temperature (step c). In step (d) the adduct obtained in step (c) is cyclizised in HC to obtain the substituted imidazolyl-moiety.

Intermediate compounds of Formula (III) may be prepared from compounds according to Formula (I-c) by selectively reducing the alkyloxycarbonyl-moiety of the piperidinyl-moiety according to the following reaction:

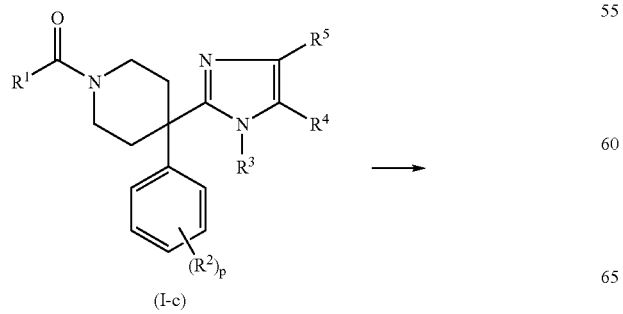

(I-c)

-continued

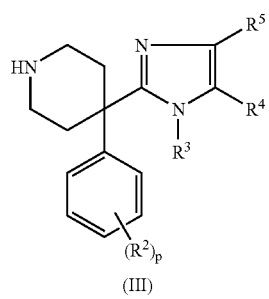

(III)

The reaction is performed in the presence of a suitable base, such as KOH, in a suitable reaction-inert solvent, such as 2-propanol and at reflux temperature.

Intermediate compounds according to Formula (IV) may be prepared by hydrogenating compounds according to Formula (I-c) according to the following reaction:

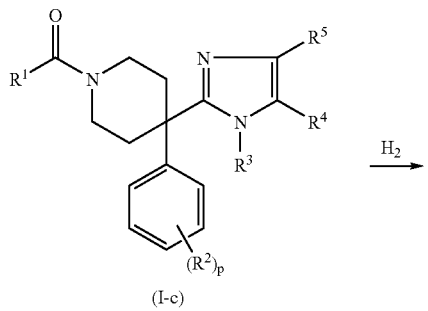

(I-c)

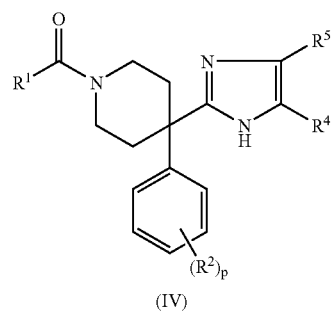

(IV)

wherein all variables are defined as in Formula (I). The reaction is performed in the presence of a catalyst, such as Pd/C (10%) in methanol at a moderately elevated temperature.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC.

The following examples illustrate the present invention without being limited thereto.

Experimental Part

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The isolation method is described in detail below.

Hereinafter, "DMF" is defined as N,N-dimethylformamide, 'THF' is defined as tetrahydrofuran and "DIPE" is defined as diisopropyl ether.

A. PREPARATION OF THE INTERMEDIATE COMPOUNDS

EXAMPLE A1

1-Methyl-4-phenyl-4-piperidinecarbonyl chloride (0.49 mol) was added portionwise at room temperature to a stirring mixture of benzenemethanamine (0.49 mol) and N,N-diethylethanamine (1.223 mol) in $CH_2Cl_2$ (2500 ml). The mixture was stirred at room temperature for 1 hour. $K_2CO_3$ (150 g) and $H_2O$ were added. The mixture was stirred and separated into its layers. The aqueous layer was extracted with $CH_2Cl_2$. The combined organic layer was dried ($MgSO_4$), filtered and the solvent was evaporated. Yielding: 144 g (95%) of 1-methyl-4-phenyl-N-(phenylmethyl)-4-piperidinecarbox-amide (interm. 1).

EXAMPLE A2

A mixture of intermediate 1 (0.47 mol) in $SOCl_2$ (750 ml) was stirred and refluxed for 1 hour. The solvent was evaporated. Toluene was added twice and evaporated again. Yielding: 190 g (100%) of N-[chloro(1-methyl-4-phenyl-4-piperidinyl)methylene]-benzenemethanamine monohydrochloride (interm. 2).

EXAMPLE A3

A mixture of intermediate 2 (0.47 mol) in DMF (750 ml) was cooled on an ice bath. 2,2-Dimethoxyethanamine (0.54 mol) dissolved in DMF was added dropwise. The mixture was stirred at room temperature overnight. The solvent was evaporated. Yielding: 210 g (100%) of N-(2,2-dimethoxyethyl)-1-methyl-4-phenyl-N'-(phenylmethyl)-4-piperidinecarboximidamide dihydrochloride (interm. 3).

EXAMPLE A4

A mixture of intermediate 3 (0.47 mol) in 6N HCl (1500 ml) was stirred until a cloudy solution, then washed with $CH_2Cl_2$ (900 ml), stirred at 80° C. for 1 hour, cooled, alkalized with a NaOH 50% solution and extracted with $CH_2Cl_2$. The organic layer was separated, dried ($MgSO_4$), filtered and the solvent was evaporated. The residue was crystallized from $CH_3CN$. The precipitate was filtered off and dried. Yielding: 38.3 g (25%) of 1-methyl-4-phenyl-4-[1-(phenylmethyl)-1H-imidazol-2-yl]piperidine (interm. 4).

EXAMPLE A5

A mixture of Compound 1 (0.089 mol) in methanol (250 ml) was hydrogenated at 50° C. with Pd/C 10% (3 g) as a catalyst. After uptake of hydrogen (1 equiv), the catalyst was filtered off and the filtrate was evaporated. The residue was crystallized from $CH_3CN$. The precipitate was filtered off and dried. Yielding: 23.89 g (90%) of ethyl 4-phenyl-4-(1H-imidazol-2-yl)-1-piperidinecarboxylate (interm. 5).

EXAMPLE A6

A mixture of intermediate 5 (0.026 mol) and KOH (0.26 mol) in 2-propanol (150 ml) was stirred and refluxed for 10 hours. The solvent was evaporated. The residue was taken up in $H_2O$ and the mixture was extracted with $CH_2Cl_2$. The organic layer was separated, dried, filtered and the solvent was evaporated. Yielding: 9.4 g of 4-phenyl-4-[1-(phenylmethyl)-1H-imidazol-2-yl]piperidine (interm. 6).

EXAMPLE A7

Reaction under $N_2$ atmosphere. A mixture of intermediate 5 (0.0033 mol) in DMF (5 ml) and THF (5 ml) was added dropwise to a solution of NaH, 60% in mineral oil (0.004 mol) in THF (10 ml), stirred at room temperature. The mixture was stirred for one hour at room temperature. Then, a solution of 4-(acetyloxy)benzenemethanol (0.004 mol) in THF was added dropwise and the resulting reaction mixture was extracted with $CH_2Cl_2$. The separated organic layer was dried ($Na_2SO_4$), filtered and the solvent was evaporated. The residue was purified by short open column chromatography over silica gel (eluent: $CH_2Cl_2/(CH_3OH/NH_3)$ 95/5). The pure fractions were collected and the solvent was evaporated. Yielding: 1.33 g of ethyl 4-phenyl-4-[1-((4-methylcarboxy) phenylmethyl)-1H-imidazol-2-yl]-1-piperidinecarboxylate (interm. 7).

B. PREPARATION OF THE FINAL COMPOUNDS

EXAMPLE B1

A mixture of intermediate 4 (0.05 mol) and N,N-diethylethanamine (0.15 mol) in toluene (750 ml) was stirred at 100° C. Ethyl chloroformate (0.25 mol) was added dropwise and the reaction mixture was stirred and refluxed for 1 hour and then cooled. The mixture was poured out into an aqueous $K_2CO_3$ solution (35 g $K_2CO_3$). The layers were separated. The water layer was extracted with $CH_2Cl_2$. The separated organic layer was dried ($MgSO_4$), filtered and the solvent evaporated. The residue was purified over silica gel on a glass filter (eluent: $CH_2Cl_2/C_2H_5OH$ 98/2). The desired fractions were collected and the solvent was evaporated. The residue was crystallized from $CH_3CN$, filtered off and dried. Yielding: 16.7 g (86%) of ethyl 4-phenyl-4-[1-(phenylmethyl)-1H-imidazol-2-yl]-1-piperidinecarboxylate (Compound 1).

EXAMPLE B2

The Preparation of Compound 2

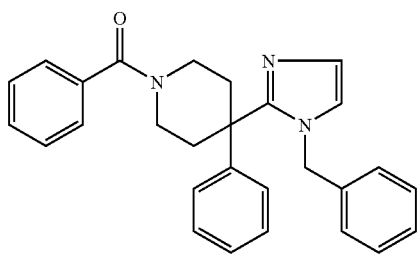

Benzoyl chloride (0.0023 mol) was added to a mixture of intermediate 6 (0.0019 mol) and N,N-diethylethanamine (0.0024 mol) in $CH_2Cl_2$ (15 ml), stirred at room temperature. The reaction mixture was stirred for 30 min at room temperature. Water was added. The layers were separated. The aqueous layer was extracted with $CH_2Cl_2$. The combined organic layers were dried ($Na_2SO_4$), filtered and the solvent evaporated. The residue was purified by short open column chromatography over silica gel (eluent: $CH_2Cl_2/(CH_3OH/NH_3)$ 98/2). The pure fractions were collected and the solvent was evaporated. The residue was recrystallized from n-hexane, filtered off and dried. Yield: 0.42 g (52%) of Compound 2; mp. 122.7° C.

EXAMPLE B3

The Preparation of Compound 3

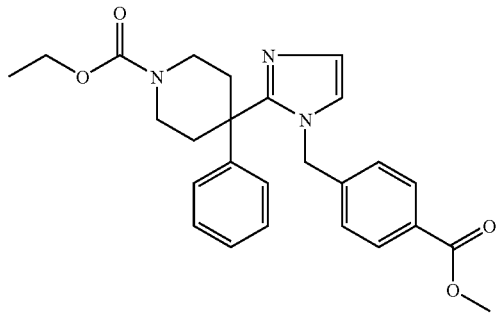

Reaction under $N_2$ atmosphere. A solution of intermediate 5 (0.0054 mol) in DMF (10 ml) and THF (10 ml) was added dropwise to NaH (0.00624 mol) in THF (30 ml) and the mixture was stirred at room temperature for 1 hour. Then, methyl 4-(bromomethyl)benzoate (0.00624 mol) in THF (5 ml) was added dropwise and the reaction mixture was stirred at 60° C. for 3 hours. Water was added and the mixture was extracted with $CH_2Cl_2$. The combined organic layers were dried ($Na_2SO_4$), filtered and the solvent was evaporated. The residue was purified by short open column chromatography over silica gel (eluent: $CH_2Cl_2/(CH_3OH/NH_3)$ 98/2). The desired fractions were collected and the solvent was evaporated. The residue was crystallized from DIPE, filtered off and dried. Yield: 1.7 g (70%) of Compound 3; mp. 149.1° C.

EXAMPLE B4

The Preparation of Compound 4

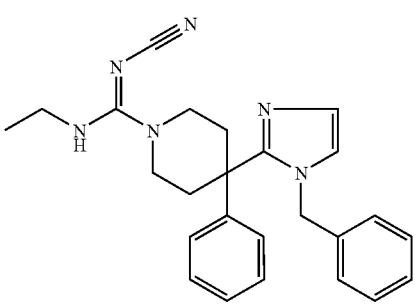

A mixture of intermediate 6 (0.0059 mol) and

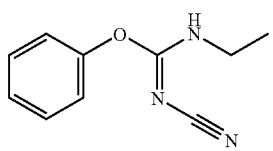

(0.0059 mol) in $CH_3CN$ (70 ml) was stirred and refluxed for 24 hours. The solvent was evaporated. Water was added. This mixture was extracted with CH$_2$Cl$_2$. The separated organic layer was dried (Na$_2$SO$_4$, anhydrous), filtered and the solvent was evaporated. The residue was crystallized from DIPE, filtered off and recrystallized from CH$_3$CN, filtered off and dried. Yield: 0.33 g of Compound 4; mp. 84.2° C.

EXAMPLE B5

The Preparation of Compound 5

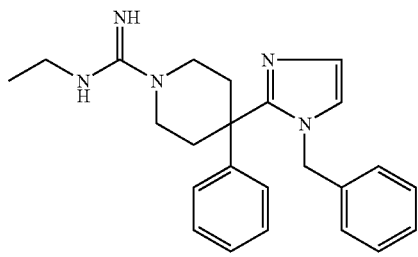

A mixture of Compound 4 (0.0001 mol) in HCl 6N (22.8 ml) was stirred and refluxed for 4 hours. The reaction mixture was alkalized, then extracted with CH$_2$Cl$_2$. The separated organic layer was dried (Na$_2$SO$_4$, anhydrous), filtered and the solvent was evaporated. The residue was recrystallized from DIPE, filtered off and dried. Yield: 0.24 g (62%) of Compound 5.

EXAMPLE B6

The Preparation of Compound 6

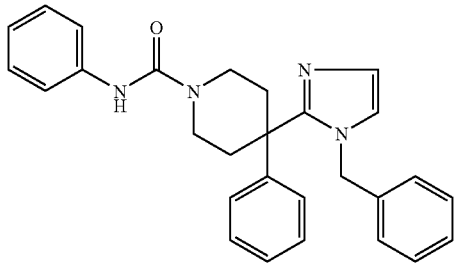

Isocyanatobenzene (0.0094 mol) was added dropwise to intermediate 6 (0.0094 mol) in THF (50 ml) and the reaction mixture was stirred for 30 min at room temperature. Water was added and this mixture was extracted with CH$_2$Cl$_2$. The separated organic layer was dried (Na$_2$SO$_4$), filtered and the solvent evaporated. The solid residue was washed with 2-propanone, filtered off and dried. Yield: 2.7 g (68%) of Compound 6.

EXAMPLE B7

The Preparation of Compound 7

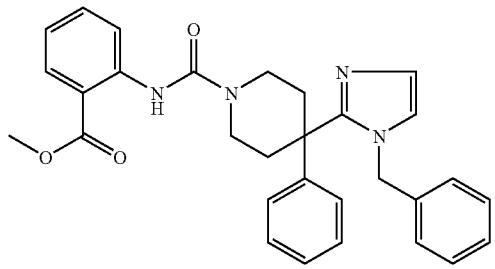

Methyl 2-isocyanatobenzoate (0.0007 mol) was added to intermediate 6 (0.0007 mol) in THF (10 ml) and the reaction mixture was stirred for 3 hours at room temperature. Water was added and this mixture was extracted with CH$_2$Cl$_2$. The separated organic layer was dried (Na$_2$SO$_4$), filtered and the solvent evaporated. The residue (0.4 g) was purified by HPLC over silica gel (eluent: CH$_2$Cl$_2$/CH$_3$OH 98/2). The desired fractions were collected and the solvent was evaporated. Yield: 0.2 g (66%) of Compound 7.

EXAMPLE B8 a) The Preparation of Compound 8

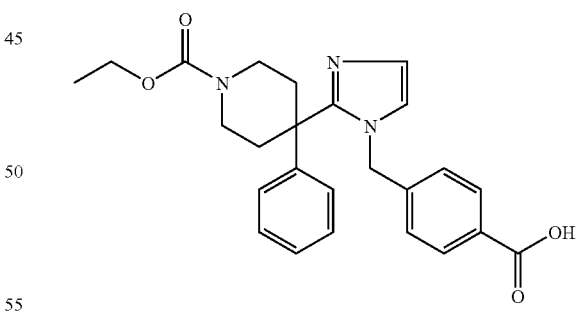

A mixture of Compound 3 (0.002 mol) and LiOH (0.02 mol) in THF (11 ml) and H$_2$O (11 ml) was stirred at room temperature for 24 hours. H$_2$O was added. The mixture was brought to pH 6 and then extracted with CH$_2$Cl$_2$. The organic layer was separated, dried, filtered and the solvent was evaporated. The residue was washed with CH$_2$Cl$_2$. Yielding: 0.72 g (83%) of Compound 8; mp. 251.6° C.

b) The Preparation of Compound 9

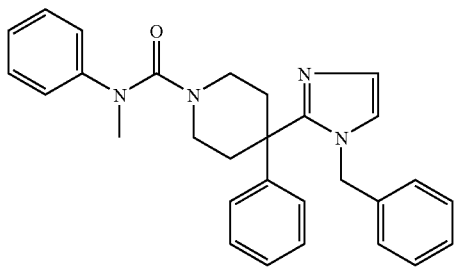

Reaction under N₂ atmosphere. A solution of NaH 60% (0.000642 mol) in DMF (2 ml) was stirred at room temperature. A solution of Compound 6 (0.000642 mol) in DMF (8 ml) was added dropwise and the reaction mixture was stirred for one hour at room temperature. CH₃I (0.001284 mol) was added and the reaction mixture was stirred at 60° C. in a Parr pressure vessel for 2 hours. The solvent was evaporated. The residue was purified by high-performance liquid chromatography over silica gel (eluent: CH₂Cl₂/CH₃OH 98/2). The desired fractions were collected and the solvent was evaporated. Yield: 0.14 g (49%) of Compound 9.

c) The Preparation of Compound 10

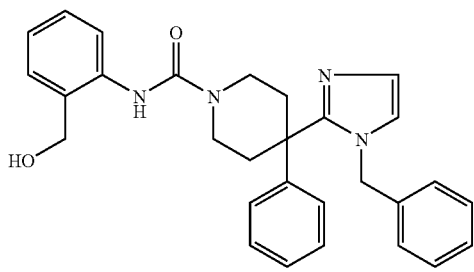

LiAlH₄ 1M in THF (0.000444 mol) was added dropwise to a solution of Compound 7 (0.000404 mol) in THF (5 ml), stirred at 0° C. The reaction mixture was stirred for 30 min at 0° C. The mixture was treated with a 10% aqueous NH₄Cl solution and extracted with EtOAc. The separated organic layer was dried (Na₂SO₄), filtered and the solvent evaporated. The residue was purified by CC-TLC on Chromatotron (eluent: CH₂Cl₂/CH₃OH 96/4). The desired fractions were collected and the solvent was evaporated. The residue was crystallized from CH₃OH/H₂O, filtered off and dried. Yield: 0.020 g (10%) of Compound 10.

d) The Preparation of Compound 11

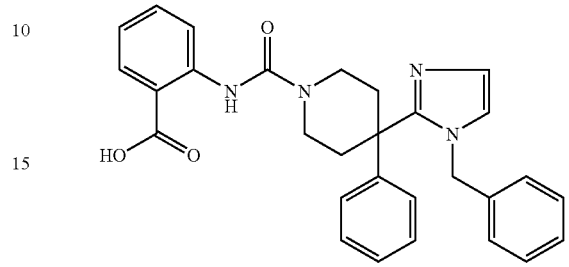

LiOH (0.001423 mol) was added portionwise to a solution of Compound 7 (0.0006469 mol) in dixoane/H₂O 1/1 (6 ml). The resulting suspension was stirred for 18 hours at room temperature. The solvent was evaporated. The residue was taken up into water and extracted with a mixture of EtOAc and 1-butanol. The organic layer was separated, dried (Na₂SO₄), filtered and the solvent was evaporated. The residue was taken up into 1 N HCl, then extracted with EtOAc. The organic layer was separated, washed with brine, dried (Na₂SO₄), filtered and the solvent was evaporated. The residue was crystallized from Et₂O/CH₂Cl₂, filtered off and dried. Yield: 0.16 g (51%) of Compound 11.

EXAMPLE B9

LiOH (0.018 mol) was added to a mixture of intermediate 7 (0.0018 mol) in THF (10 ml) and H₂O (10 ml). The reaction mixture was stirred for 3 hours at room temperature. Water was added. CH₂Cl₂ was added. The reaction mixture was extracted. The organic layer was separated, dried (Na₂SO₄), filtered and the solvent was evaporated. The white solid residue was washed with methanol and CH₂Cl₂, then dried. Yielding: 0.54 g of ethyl 4-phenyl-4-[1-(4-hydroxyphenylmethyl)-1H-imidazol-2-yl]-1-piperidinecarboxylate (Compound 12).

The following compounds as listed in Tables 1-5 were prepared: (All melting points (m.p.) in ° C.)

TABLE 1

| Comp. nr. | Exp. nr. | R¹— | R³— | Phys. prop. |
|---|---|---|---|---|
| 110 | B2 | —H | 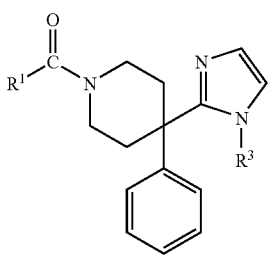 | |

TABLE 1-continued
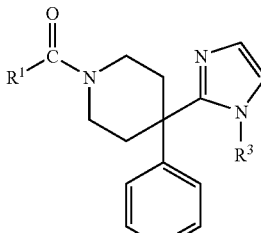
| Comp. nr. | Exp. nr. | R¹— | R³— | Phys. prop. |
|---|---|---|---|---|
| 13 | B1 | methoxy | benzyl | |
| 14 | B3 | ethoxy | cyclohexylmethyl | m.p. = 137 |
| 1 | B1 | ethoxy | benzyl | |
| 12 | B9 | ethoxy | 4-hydroxybenzyl | |
| 15 | B3 | ethoxy | 4-methoxybenzyl | |
| 16 | B3 | ethoxy | 4-fluorobenzyl | m.p. = 117 |
| 17 | B3 | ethoxy | 3-fluorobenzyl | m.p. = 127 |
| 18 | B3 | ethoxy | 3-methoxybenzyl | m.p. = 125 |
| 8 | B6 | ethoxy | 4-carboxybenzyl | m.p. = 252 |
| 3 | B3 | ethoxy | 4-(methoxycarbonyl)benzyl | m.p. = 149 |

TABLE 1-continued
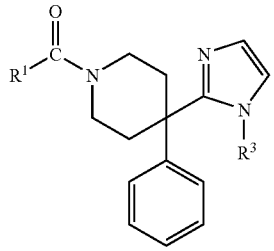
| Comp. nr. | Exp. nr. | R¹— | R³— | Phys. prop. |
|---|---|---|---|---|
| 19 | B3 | 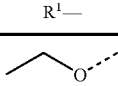 | 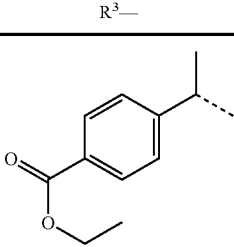 | |
| 20 | B3 | 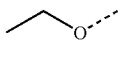 | 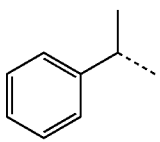 | |
| 21 | B3 | 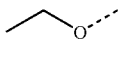 | 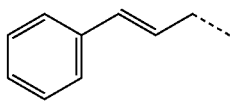 | |
| 22 | B3 | 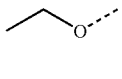 | 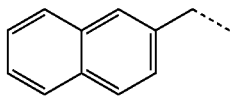 | |
| 23 | B3 | 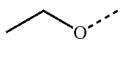 | 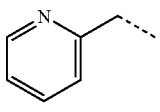 | m.p. = 199 |
| 112 | B3 | 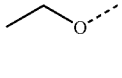 | 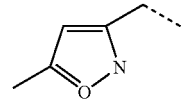 | m.p. = 128 |
| 24 | B1 | 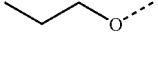 | 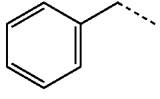 | m.p. = 130 |
| 25 | B1 | 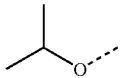 | 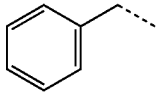 | m.p. = 160 |
| 26 | B2 | 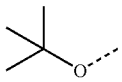 | 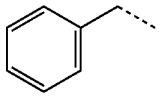 | m.p. = 133 |
| 27 | B1 | 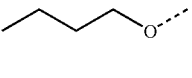 | 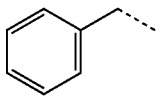 | m.p. = 80 |

TABLE 1-continued
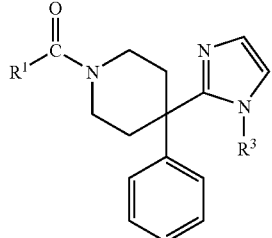
| Comp. nr. | Exp. nr. | R¹— | R³— | Phys. prop. |
|---|---|---|---|---|
| 28 | B1 | 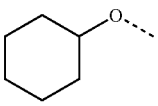 | 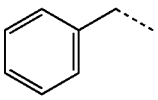 | m.p. = 215 |
| 29 | B2 | 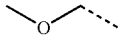 | 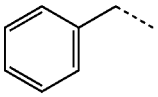 | m.p. = 111 |
| 30 | B3 | 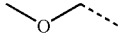 | 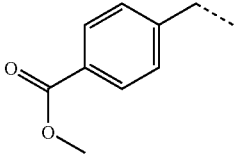 | |
| 31 | B3 | 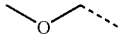 | 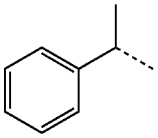 | |
| 32 | B1 | 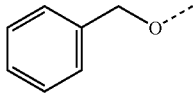 | 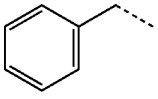 | |
| 33 | B2 | CH₃— | 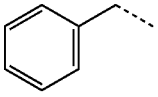 | m.p. = 183 |
| 34 | B2 | CH₃CH₂— | 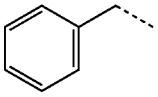 | m.p. = 133 |
| 35 | B2 | isopropyl- | 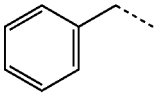 | m.p. = 107 |
| 36 | B2 |  | 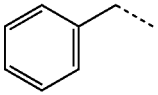 | m.p. = 111 |
| 37 | B2 | tert-butyl- | 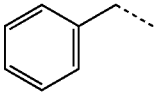 | m.p. = 165 |

TABLE 1-continued
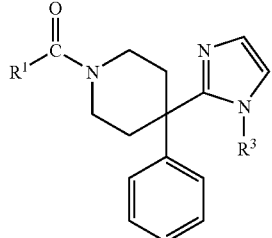
| Comp. nr. | Exp. nr. | R¹— | R³— | Phys. prop. |
| --- | --- | --- | --- | --- |
| 2 | B2 | phenyl | benzyl | m.p. = 123 |
| 38 | B3 | phenyl | 4-(methoxycarbonyl)benzyl | |
| 39 | B3 | phenyl | 4-(methoxycarbonyl)benzyl | |
| 40 | B3 | phenyl | 4-(N,N-diethylcarbamoyl)benzyl | |
| 41 | B3 | phenyl | 1-phenylethyl | |
| 42 | B2 | 3,5-bis(trifluoromethyl)phenyl | benzyl | m.p. = 151 |
| 43 | B2 | 3,5-dimethylphenyl | benzyl | m.p. = 79 |
| 44 | B2 | 2,4,6-trimethylphenyl | benzyl | m.p. = 149 |

TABLE 1-continued

| Comp. nr. | Exp. nr. | R¹— | R³— | Phys. prop. |
|---|---|---|---|---|
| 45 | B2 | benzyl | benzyl | |
| 46 | B2 | NH₂— | benzyl | m.p. = 208 |
| 47 | B2 | ethyl-NH— | benzyl | m.p. = 144 |
| 48 | B2 | ethoxycarbonylmethyl-NH— | benzyl | |
| 49 | B2 | tert-butyl-NH— | benzyl | |
| 50 | B2 | n-butyl-NH— | benzyl | |
| 51 | B2 | cyclohexyl-NH— | benzyl | |
| 6 | B6 | phenyl-NH— | benzyl | |
| 52 | B3 | phenyl-NH— | 4-(methoxycarbonyl)benzyl | |
| 53 | B3 | phenyl-NH— | naphthalen-2-ylmethyl | |

TABLE 1-continued

| Comp. nr. | Exp. nr. | R¹— | R³— | Phys. prop. |
|---|---|---|---|---|
| 54 | B3 | C₆H₅-NH- | cyclohexylmethyl | |
| 55 | B3 | C₆H₅-NH- | 1-phenylethyl | |
| 56 | B3 | C₆H₅-NH- | 2-fluorobenzyl | |
| 57 | B3 | C₆H₅-NH- | 3-methoxybenzyl | |
| 58 | B3 | C₆H₅-NH- | 3-fluorobenzyl | |
| 59 | B3 | C₆H₅-NH- | (pyridin-2-yl)methyl | |
| 60 | B3 | C₆H₅-NH- | benzoyl | |
| 61 | B3 | C₆H₅-NH- | 4-(methylsulfonyl)benzyl | |
| 62 | B3 | C₆H₅-NH- | 4-fluorobenzyl | |

TABLE 1-continued
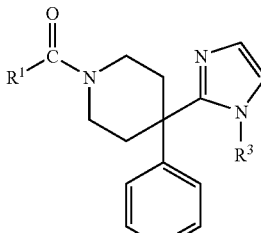
| Comp. nr. | Exp. nr. | R¹— | R³— | Phys. prop. |
|---|---|---|---|---|
| 63 | B3 | 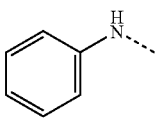 | 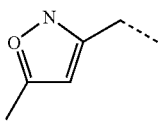 | |
| 64 | B2 | 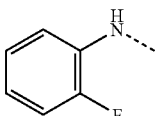 | 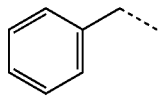 | |
| 65 | B2 | 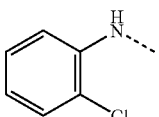 | 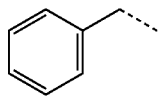 | |
| 66 | B2 | 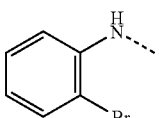 | 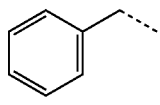 | |
| 67 | B2 | 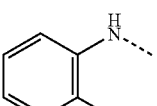 | 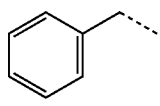 | |
| 68 | B2 | 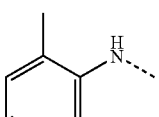 | 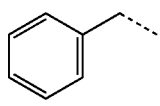 | |
| 7 | B7 | 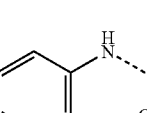 | 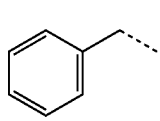 | |
| 69 | B2 | 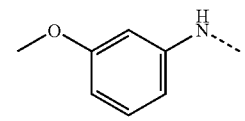 | 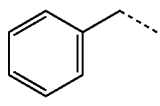 | |
| 7 | B2 | 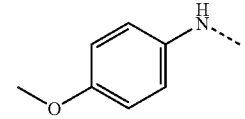 | 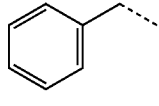 | |

TABLE 1-continued
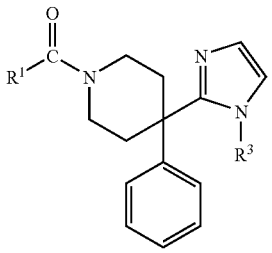
| Comp. nr. | Exp. nr. | R¹— | R³— | Phys. prop. |
|---|---|---|---|---|
| 70 | B2 | 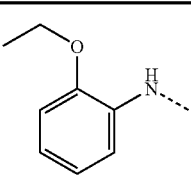 | 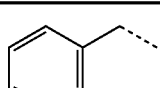 | |
| 71 | B2 | 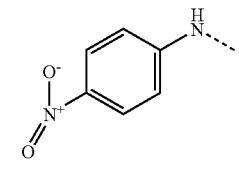 | 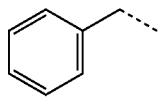 | |
| 72 | B2 | 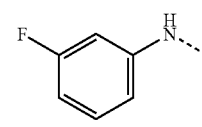 | 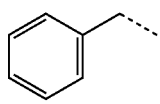 | |
| 73 | B2 | 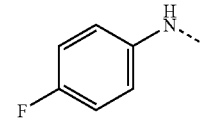 | 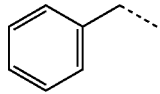 | |
| 74 | B2 | 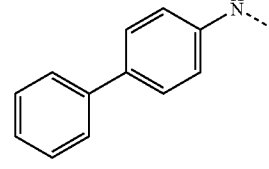 | 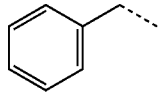 | |
| 10 | B6 | 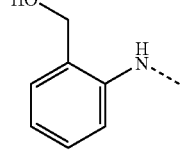 | 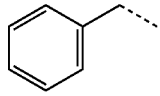 | |
| 75 | B2 | 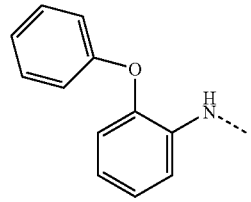 | 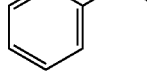 | |

TABLE 1-continued
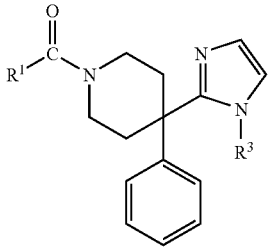
| Comp. nr. | Exp. nr. | R¹— | R³— | Phys. prop. |
|---|---|---|---|---|
| 76 | B2 | 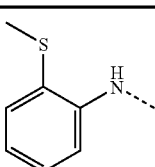 | 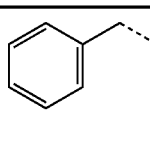 | |
| 77 | B2 | 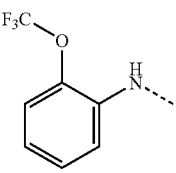 | 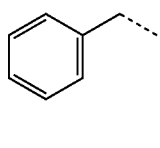 | |
| 11 | B6 | 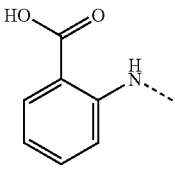 | 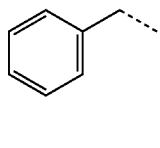 | |
| 78 | B2 | 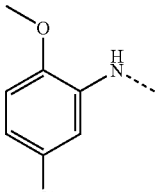 | 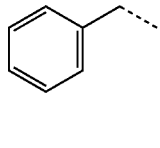 | |
| 79 | B2 | 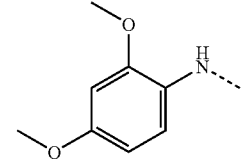 | 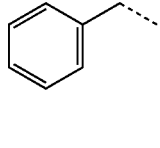 | |
| 9 | B6 | 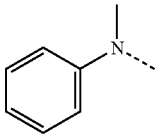 | 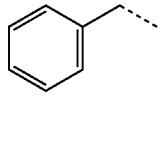 | |
| 80 | B2 | 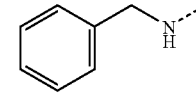 | 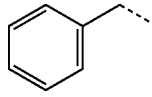 | |
| 81 | B2 | 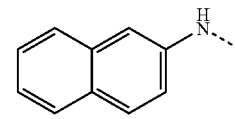 | 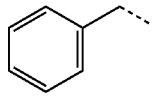 | |

TABLE 1-continued
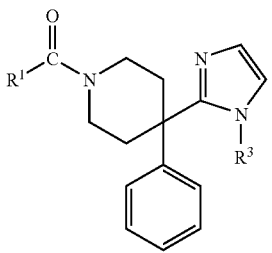
| Comp. nr. | Exp. nr. | R¹— | R³— | Phys. prop. |
|---|---|---|---|---|
| 113 | B2 | 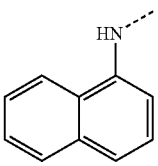 | 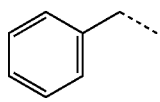 | |
| 82 | B2 | 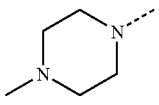 | 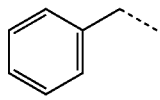 | |
| 83 | B2 | 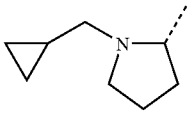 | 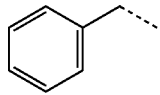 | m.p. = 74 |
| 84 | B2 | 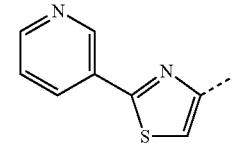 | 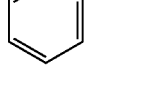 | |
| 85 | B2 | 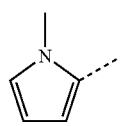 | 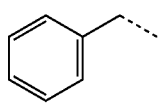 | m.p. = 165 |
| 86 | B2 | 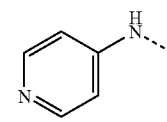 | 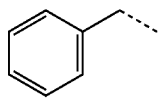 | |
| 87 | B2 | 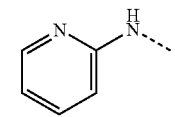 | 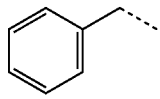 | |

TABLE 2

| Comp. nr. | Exp. nr. | Rᵃ— | Rᵇ— | R²— | Position of R² | Phys. data |
|---|---|---|---|---|---|---|
| 88 | B3 | phenyl | H | —O—CH₃ | c | |
| 89 | B3 | phenyl | H | —F | c | |
| 90 | B3 | phenyl | H | —F | a | |
| 114 | B3 | phenyl | phenyl | — | — | |
| 115 | B3 | phenyl | H | — | — | |

TABLE 3

| Comp. nr. | Exp. nr. | A=B | R¹— | Phys. data |
|---|---|---|---|---|
| 5 | B5 | C=NH | ethyl-NH | |
| 91 | B5 | C=N—H | phenyl-NH | |
| 4 | B4 | C=N—CN | ethyl-NH | m.p. = 84 |
| 92 | B4 | C=N—CN | phenyl-NH | |
| 93 | B4 | C=C—NO₂ | phenyl-NH | |

TABLE 3-continued
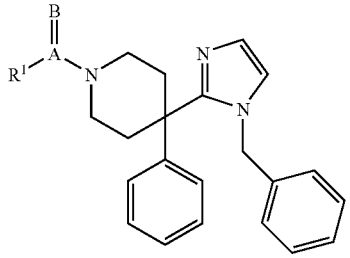
| Comp. nr. | Exp. nr. | A=B | R¹— | Phys. data |
|---|---|---|---|---|
| 95 | B2 | C=S | 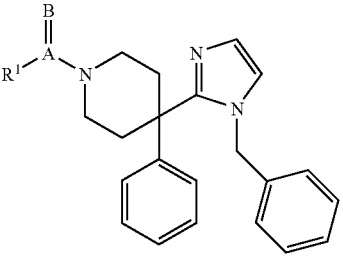 | m.p. = 172 |
| 96 | B2 | C=S | 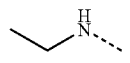 | |
| 94 | B2 | SO₂ | —CH₃ | m.p. = 167 |
TABLE 3-continued
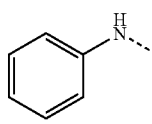
| Comp. nr. | Exp. nr. | A=B | R¹— | Phys. data |
|---|---|---|---|---|
| 97 | B2 | SO₂ | —NH₂ | m.p. = 212 |
| 111 | B2 | SO₂ | —CF₃ | m.p. = 104 |
| 98 | B2 | SO₂ | 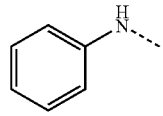 | |
TABLE 4
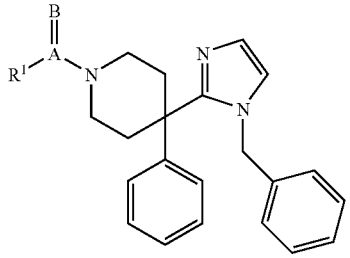
| Comp. nr. | Exp. nr. | Z (A=B and R¹ together) | R³— | Phys. data |
|---|---|---|---|---|
| 99 | B3 | 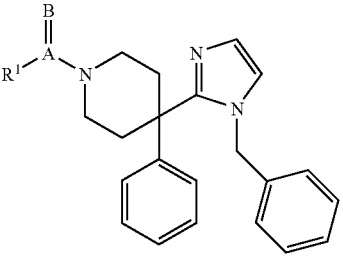 | 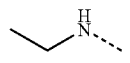 | |
| 100 | B3 | 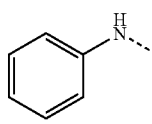 | 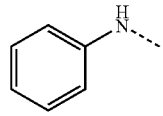 | |
| 101 | B3 | 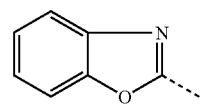 | 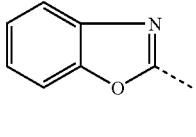 | |
| 102 | B3 | 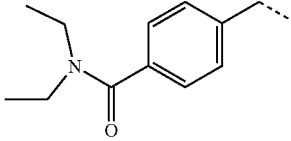 | 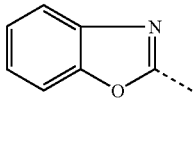 | |
| 103 | B2 | 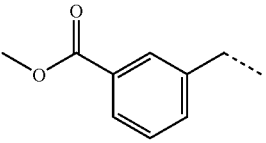 | 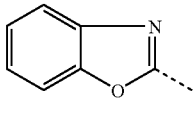 | m.p. = 204 |

TABLE 4-continued

| Comp. nr. | Exp. nr. | Z (A=B and R¹ together) | R³— | Phys. data |
|---|---|---|---|---|
| 104 | B2 | benzimidazole (N-methyl) | phenyl | m.p. = 181 |
| 105 | B2 | thiazole | phenyl | m.p. = 190 |
| 106 | B2 | benzothiazole | phenyl | m.p. = 107 |

TABLE 5

| Comp. nr. | Exp. nr. | R¹— | Phys. data |
|---|---|---|---|
| 107 | B3 | —OH | |
| 108 | B2 | —N(Et)₂ | m.p. = 105 |
| 109 | B2 | —NH₂ | m.p. = 136 |

C. PHARMACOLOGICAL EXAMPLES

The pharmacological properties were examined for radioligand binding as well as GTPγS binding assays, of the selected compounds on the cloned human δ, κ and μ opioid receptors, expressed in a mammalian cell line. Second messenger signaling was measured on membrane preparations via stimulation of [$^{35}$S]GTPγS binding. In this functional assay, agonistic and antagonistic properties of the compounds were investigated.

DPDPE ((D-Pen$^{2,5}$)enkephalin) was used as the reference agonist and naltrindole as the reference antagonist for the δ opioid receptor (Malatynska E., Wang Y., Knapp R. J., Santoro G., Li X, Waite S., Roeske W. R., Yamamura H. I.: *Human δ opioid receptor: a stable cell line for functional studies of opioids. NeuroReport* 6, 613-616, 1995) and (Portoghese P. S., Sultana M., Takemori A. E.: *Naltrindole, a highly selective and potent non-peptide δ opioid receptor antagonist. Eur. J. Pharmacol.* 146, 185-186, 1988) and U69593 and nor-binaltorphimine (nor-BNI) were used for the κ opioid receptor as the reference agonist and antagonist, respectively. For the μ opioid receptor, morphine was used as the reference agonist and naloxone as the reference antagonist (Alt A., Mansour A., Akil H., Medzihradsky F., Traynor J. R., Woods J. H.: *Stimulation of guanosine-5'-O-(3-[$^{35}$S]thio) triphosphate binding by endogenous opioids acting at a cloned Mu receptor. J. Pharmacol. Exp. Ther.* 286, 282-288, 1998) and (Smart D., Hirst R. A., Hirota K., Grandy D. K, Lambert D. G.: *The effects of recombinant rat μ-opioid receptor activation in CHO cells on phospholipase C, [Ca$^{2+}$]I and adenylyl cyclase. Br. J. Pharmacol.* 120, 1165-1171, 1997).

C.1. Materials and Methods

Cell Culture

CHO cells, permanent transfected with the κ or μ opioid receptor, were cultured in Dulbecco's modified Eagle's medium (DMEM)/Nutrient mixture Ham's F12 (ratio 1:1) supplemented with 10% heat inactivated fetal calf serum, and an antibiotic solution containing 100 IU/ml penicillin G, 100 μg/ml streptomycin sulfate, 110 μg/ml pyruvic acid and 300 μg/ml L-glutamine. C6 glioma cells, permanent transfected with the δ opioid receptor, required a DMEM medium, enriched with 10% heat inactivated fetal calf serum and the antibiotic solution as described above.

Membrane Preparation

The membranes were prepared as total particulate fractions. All cell lines were cultured to 90% confluency on 145 mm Petri dishes and treated with 5 mM sodium butyrate, 24 hours before collection. The culturing medium was removed and the cells were washed with ice cold phosphate buffered saline (PBS w/o Ca$^{2+}$ and Mg$^{2+}$), scraped from the plates in 50 mM Tris-HCl buffer, pH 7.4, and collected through centrifugation (10 minutes at 16,000 RPM at 4° C.). The cell pellet was re-suspended in hypotonic 5 mM Tris-HCl buffer, pH 7.4, and re-homogenized with an Ultra Turrax homogenizer. The homogenate was centrifuged at 18000 RPM for 20 minutes at 4° C. The final pellet was re-suspended in 50 mM Tris-HCl buffer, pH 7.4 and stored in aliquots at −70° C. A protein determination was performed using the Biorad protein assay (Bradford) using bovine serum albumine (BSA) as a standard (Bradford, M. M.: *A rapid and sensitive method for the quantification of microgram quantities of protein utilizing the principle of protein-dye binding. Analytical Biochem.* 72: 248-254, 1976).

C.2. Radioligand Binding

Preliminary radioligand binding experiments were carried out to reveal the optimal assay conditions for these opioid receptor subtypes in their corresponding mammalian cell membranes.

Competitive inhibition of [$^3$H]DPDPE by the compounds was performed with a concentration of the radioligand of 2 nM ($K_d$=1.7 nM) and various concentrations in singlet of the compounds, spanning at least 3 orders of magnitude around the pIC$_{50}$ value. For competition binding on the κ and μ receptor, [$^3$H]U69593 ($K_d$=0.4 nM) and [$^3$H]DAMGO ($K_d$=0.6 nM) were used respectively at a concentration of 1 nM. Membranes were thawed on ice and diluted in a 50 mM Tris-HCl buffer, pH 7.4. For the δ opioid receptor, this incubation buffer was supplemented with 2 mM MgCl$_2$, 1 mM EGTA and 0.1% BSA. Non-specific binding was defined in the presence of 1 μM of naltrindole, spiradoline and dextromoramide for the δ, κ, and μ opioid receptor, respectively. An incubation of 1 hour at 25° C. was found to be optimal for competition binding assays for all the three receptor subtypes. The assays were carried out in a final volume of 500 μl. The reaction was terminated by rapid filtration over an UniFilter™-96, GF/B™ under reduced pressure using Filtermate 196 (Packard). The amount of bound radioactivity on the filter unit was determined after filter drying and scintillant addition (Microscint-O; Packard) by liquid scintillation counting.

C.3. [$^{35}$S]GTPγS Binding

Determination of [$^{35}$S]GTPγS binding to the G-proteins was carried out with a modified procedure of Lazareno (Lazareno S.: *Measurement of agonist-stimulated [$^{35}$S]GTPγS binding to cell membranes. Meth. Molec. Biol.* 106, 231-243, 1999).

In preliminary [$^{35}$S]GTPγS binding experiments, assay conditions were optimized which resulted in the choice of the following buffers: 20 mM Hepes with 100 mM NaCl, containing 3 μM GDP and 1 mM MgCl$_2$ for the μ opioid receptor CHO membranes, containing 10 μM GDP and 1 mM MgCl$_2$ for the δ opioid receptor C6 glioma cell membranes, and 10 μM GDP and 0.3 mM MgCl$_2$ for the κ opioid receptor CHO membranes. The assay mixtures contained 10 μg of membrane protein. An additional 10 μg/ml saponine was added to the diluted membranes as a detergent to maximize the [$^{35}$S]GTPγS penetration through the membranes.

For testing agonistic activity, 175 μl of diluted membranes was pre-incubated in the buffer described above together with 25 μl of buffer and 25 μl of varying concentrations of the compound in a total volume of 225 μl. For antagonistic activities, the 25 μl of the buffer addition was replaced with the reference agonist for stimulating the basal levels. For all three cell lines, a concentration of 300 nM of DPDPE, U69593 and morphine were used for their corresponding receptor subtypes. After a 20 minutes pre-incubation period at 37° C., 25 μl of [$^{35}$S]GTPγS was added to a final concentration of 0.25 nM and the assay mixtures were further incubated for 20 minutes at 37° C. Bound and free [$^{35}$S]GTPγS were separated by rapid filtration over an UniFilter™-96, GF/B™ under reduced pressure using Filtermate 196 (Packard). The amount of bound radioactivity on the filter unit was determined after filter drying and scintillant addition (Microscint-O; Packard) by liquid scintillation counting.

Basal [$^{35}$S]GTPγS binding was measured in absence of compounds. Stimulation by agonist was calculated as the percentage increase above basal levels. The sigmoid agonist concentration response curves for increases in [$^{35}$S]GTPγS binding and antagonist inhibition curves for inhibition of the reference agonist-stimulated [$^{35}$S]GTPγS binding were analyzed by non-linear regression using the GraphPad Prism program. Data were retrieved from independent experiments and the different concentration points were run in duplicates.

C.4. Results

All compounds according to the invention showed a pIC$_{50}$ value of at least 6 for the delta opioid receptor and a pIC$_{50}$ value of 6 or less for either mu and kappa receptor.

The compounds listed in Table 6 showed a pIC$_{50}$ value of between 7 and 8 for the delta opioid receptor and a pIC$_{50}$ value of 6 or less for either mu and kappa receptor.

The compounds listed in Table 7 showed a pIC$_{50}$ value above 8 for the delta opioid receptor and a pIC$_{50}$ value of 6 or less for either mu and kappa receptor. The selectivity for the delta opioid receptor over the mu opioid receptor is as high as 600.

TABLE 6 pIC$_{50}$ values for the delta opioid receptor agonist test.

| Comp. Nr. | pIC$_{50}$ | Comp. Nr. | pIC$_{50}$ |
|---|---|---|---|
| 43 | 7.9 | 22 | 7.3 |
| 17 | 7.9 | 87 | 7.3 |
| 30 | 7.9 | 45 | 7.3 |
| 105 | 7.9 | 51 | 7.3 |
| 78 | 7.9 | 4 | 7.3 |
| 101 | 7.8 | 55 | 7.3 |
| 28 | 7.8 | 71 | 7.3 |
| 11 | 7.8 | 99 | 7.3 |
| 29 | 7.8 | 34 | 7.2 |
| 67 | 7.8 | 72 | 7.2 |
| 7 | 7.7 | 81 | 7.2 |
| 9 | 7.7 | 64 | 7.2 |
| 52 | 7.7 | 18 | 7.2 |
| 103 | 7.7 | 42 | 7.2 |
| 26 | 7.7 | 10 | 7.2 |
| 27 | 7.7 | 33 | 7.1 |
| 15 | 7.6 | 37 | 7.1 |
| 69 | 7.6 | 80 | 7.1 |
| 50 | 7.6 | 90 | 7.1 |
| 32 | 7.6 | 56 | 7.1 |
| 93 | 7.5 | 47 | 7.1 |
| 65 | 7.5 | 43 | 7.1 |
| 84 | 7.5 | 48 | 7.1 |
| 66 | 7.5 | 79 | 7.0 |
| 75 | 7.4 | 111 | 7.0 |
| 13 | 7.4 | 7 | 7.0 |
| 76 | 7.4 | 68 | 7.0 |
| 96 | 7.4 | 95 | 7.0 |
| 94 | 7.4 | 92 | 7.0 |
| 70 | 7.4 | 49 | 7.0 |
| 36 | 7.3 | 74 | 7.0 |

TABLE 7

Results for the agonist receptor binding (pIC$_{50}$) and signal transport binding (pIC$_{50}$) testing.

| Comp. Nr. | Formula | Agonist receptor binding (pIC$_{50}$) | | | Signal transport binding (pIC$_{50}$) | |
|---|---|---|---|---|---|---|
| | | delta | mu | kappa | delta agonist | delta antag. |
| 3 | | 8.8 | 6 | n.d. | 7.3 | 5 |
| 38 | | 8.7 | 6 | n.d. | n.d. | n.d. |
| 20 | | 8.6 | 6 | n.d. | 7 | 5 |
| 102 | | 8.5 | 6 | n.d. | n.d. | n.d. |
| 25 | | 8.4 | 6 | n.d. | 6.9 | 5 |

TABLE 7-continued

Results for the agonist receptor binding (pIC$_{50}$) and signal transport binding (pIC$_{50}$) testing.

| Comp. Nr. | Formula | Agonist receptor binding (pIC$_{50}$) | | | Signal transport binding (pIC$_{50}$) | |
|---|---|---|---|---|---|---|
| | | delta | mu | kappa | delta agonist | delta antag. |
| 2 | | 8.3 | 6 | n.d. | 6.8 | 5 |
| 41 | | 8.3 | 6 | n.d. | n.d. | n.d. |
| 98 | | 8.2 | 5.6 | 5.8 | 6.1 | 5 |
| 19 | | 8.2 | 6 | n.d. | 6.5 | 5 |
| 24 | | 8.2 | 6 | n.d. | 6.9 | 5 |

TABLE 7-continued

Results for the agonist receptor binding (pIC$_{50}$) and signal transport binding (pIC$_{50}$) testing.

| Comp. Nr. | Formula | Agonist receptor binding (pIC$_{50}$) | | | Signal transport binding (pIC$_{50}$) | |
|---|---|---|---|---|---|---|
| | | delta | mu | kappa | delta agonist | delta antag. |
| 1 | 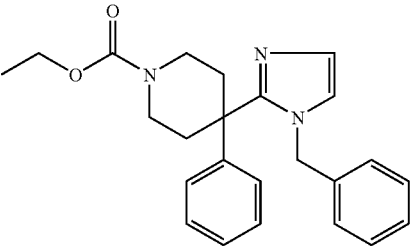 | 8.1 | 5 | 6.3 | n.d. | 5 |
| 31 | 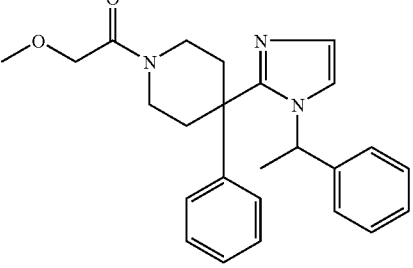 | 8.1 | 6 | n.d. | n.d. | n.d. |
| 12 | 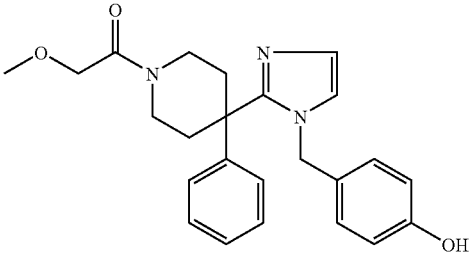 | 8.0 | 6 | n.d. | 7 | 5 | n.d.: not determined

D. CLINICAL EXPERIMENTS: CARDIAC ISCHAEMIA

D.1. Rat-Langendorff Model

Compounds Tested

The compounds 1, 24 and 25 were tested.

Model

A rat heart is rapidly dissected, attached by the aorta to a cannula and perfused with a physiological buffer (modified Krebs-Henseleit buffer: NaCl 118 mmol/l, KCl 4.7 mmol/l, MgSO$_4$ 1.2 mmol/l, KH$_2$PO$_4$ 1.2 mmol/l, CaCl$_2$ 1.8 mmol/l, NaHCO$_3$ 23 mmol/l, glucose 11 mmol/l) without blood under 80 mmHg perfusion pressure. Oxygen is dissolved in the physiological buffer. The heart is paced atrially at 350 beats per minute. A balloon that can be optionally filled (adjustment preload) is inserted into the left ventricle. Diastolic pressure and the pressure developped are measured as well as the maximal rate of pressure development as a measure of contractility (inotropism) and the minimal rate of pressure decay as a measure of relaxation. Advantages of this model are: the heart is isolated and studied in controlled circumstances without interaction with other organs and the method is reasonably rapid and cheap. Disadvantages are: no blood perfusion, with only dissolved oxygen, therefore greater coronary flow rates with considerable vasodilatation of the coronary system; a closed system without metabolism and without interaction with other organs and a small animal model, relatively far away from clinical reality.

Protocol

The study period of ischaemia is 20 minutes. The measurements after the study period of ischaemia (reperfusion phase) always last 40 minutes. Measurements before the study period of ischaemia last 30 minutes and are performed after stabilization. In the ischaemic preconditioning group the following is measured during these 30 minutes: 10 minutes baseline, 5 minutes ischaemia, 5 minutes reperfusion, 5 minutes ischaemia and 5 minutes reperfusion. In the group of the compounds according to the invention (4 µg/500 ml buffer solution) there is first 15 minutes baseline followed by 15 minutes treatment. Consequently, everything is time-matched.

Results

The recovery of the contractile function of the isolated hearts treated with the compounds according to the invention is at least as good as in the ischaemic preconditioning group.

It should be noted though that administration of the compounds according to the invention produces negative inotropic effects on the heart, as is revealed by the increase in end-diastolic pressure in the left ventricle and the decrease in the developed pressure and $dP/dt_{max}$. This may be related to the solvent cyclodextrine, since the same effect was observed in 2 experiments in which the same concentration of cyclodextrine was administered. However, the functional recovery after the study period of ischaemia was not better compared to the control group. This shows that it is not the negative inotropic effect prior to ischaemia that is cardioprotective.

Statistical analysis shows a significant change between the control group and the group treated with compounds according to the invention as regards developed pressure, end-diastolic pressure, $dP/dt_{max}$ and $dP/dt_{min}$ with $p<0.000001$ (see FIG. 1 and FIG. 2).

Ventricular fibrillation occurred during reperfusion in a significantly smaller number of rats in the group treated with the compounds according to the invention compared to the control group and also compared to the ischaemic preconditioning group. Furthermore, the number of episodes of ventricular fibrillation was smaller in the group treated with the compounds according to the invention compared to the other groups (Table 8).

TABLE 8

Results of the Rat-Langendorff experiments

| Compound Nr. | Rat Nr. | IC | $V_{fib}$ | EDP | Recup |
|---|---|---|---|---|---|
| 24 | X1 | 10 | 0 | 0 | 91% |
|  | X2 | 5 | 1 (short) | +5 | 85% |
|  | X3 | 7 | 0 | +7 | 87% |
| 25 | Y1 | 7 | 2 (short) | +10 | 75% |
|  | Y2 | 5 | 0 | +6 | 79% |
|  | Y3 | 7 | 1 (short) | +6 | 85% |
| 1 | Z1 | 4 | 0 | 0 | 92% |
|  | Z2 | 6 | 0 | +7 | 85% |
|  | Z3 | 8 | 1 (short) | +8 | 82% |
| Control | C | 21 | 4 | +26 | 48% |

IC: Ischemic contracture (mmHg)
$V_{fib}$: Number of ventricullar fibrillations during reperfusion
EDP: Degree of normalisation of EDP during reperfusion: O = recuperation to baseline EDP; + . . . mmHg = amount mmHg above baseline EDP
Recup: % recuperation in developed pressure at the end of reperfusion.

D.2 Sheep Model

To deal with the weaknesses of the previous model a complex in vivo model in sheep was used in which there was nevertheless good control over the cardiac effects.

Compounds Tested

Compound 1 was tested.

Model

The model is a sheep anaesthetized with ketamine and isoflurane. The extra corporal circulation is connected by venous cannulation of both caval veins and arterial cannulation via the carotid. An additional cannula with flow meter in the right ventricle gives the flow rate over the coronary arteries. In addition to measurements of heart rate and arterial blood pressure, the left ventricle instantaneous pressure is measured as well as the left ventricle volumes via a conductance catheter. There is also a side-tubing on the arterial cannula of the artificial heart leading to the pulmonary artery. Via this route it is possible to modulate the left ventricle preload in a perfectly controlled manner in order to obtain load-independent measurements of the left ventricle contractility before and after the study period of ischaemia. Cardiac oxygen consumption was also measured as well as regional perfusion with the aid of coloured microspheres.

The advantage of this model is that it is a large animal model, using the extra corporal circulation, in a metabolically active model, possibly with the presence of other non-cardiac effects, in well-controlled cardiac circumstances, in which the heart is perfused with blood. The technically difficult nature of the model is to be seen as a disadvantage.

Protocol

The study period of ischaemia was 30 minutes while the heart remained normothermic and was fully unloaded by the extra corporal circulation and venting of the ventricles. The control group was time-matched with the other groups. The ischaemic preconditioning group was subjected to 3 times 5 minutes of preconditioning ischaemia with 5 minute reperfusion intervals. In the three groups extra corporal circulation was started 30 minutes before the study period of ischaemia was imposed. The extra corporal circulation was stopped 40 minutes after the end of the study period of ischaemia. Compound 1 (78 mg/20 ml) was administered 15 minutes before the start of the study period of ischaemia in five technically successful experiments, whereby 10 ml of the solution was administered in one experiment and 100 ml in the four others. Only these four will be processed here. In the other groups, 7 experiments are always processed. Before each measurement of pressure-volume ratios in the left ventricle the system was switched to the right heart bypass model in which the venous flow is diverted into the extra corporal circulation via the caval veins and the blood is returned to the sheep via the pulmonary artery. This was always done during baseline, immediately after ischaemic preconditioning or the administration of Compound 1, immediately before the study period of ischaemia was imposed and 40, 70 and 100 minutes after the end of the study period of ischaemia.

Results

Conventional Parameters

No significant differences in mean blood pressure were distinguished between the groups. The administration of Compound 1 did not result in a significant change in blood pressure either. It should be noted that Compound 1 was administered in the period of extra corporal circulation, which obviously affects blood pressure.

No significant differences were observed in the left atrial pressure, though there was a tendency for the left atrial pressure to be slightly higher in the control group compared to the other two.

The same applies to cardiac flow after reperfusion with a tendency for cardiac flow to be higher in the ischaemic preconditioning group and the group treated with Compound 1.

Pressure-Volume Relationships

Pressure-volume relationships in the left ventricle were studied in the control group, the ischemic preconditioning group and the group treated with Compound 1.

As far as the load-independent parameters are concerned, the preload recruitable stroke work (PRSW, $M_{SW}$) was studied, the results of which are shown in FIG. 3. The PRSW indicates the ratio between the "stroke work" and the end-diastolic volume. The stroke work is the effective mechanical work done by the heart to eject the blood. The PRSW is greater when the same external mechanical work is done at a lower end-diastolic volume (therefore shorter sarcomere length), which is the definition of contractile state.

The PRSW is significantly better in the ischaemic preconditioning group and the group treated with Compound 1, compared to the control group after 70 and 100 minutes of reperfusion and approaches baseline value. Therefore, ischaemic preconditioning and administration of Compound 1 results in better recovery of the cardiac contractile state after 30 minutes of ischaemia in normothermic conditions during which the ventricle is unloaded.

Tau is a measure of ventricular relaxation. The lower the value of tau, the sooner ventricular relaxation occurs. This measure is important because it is known that the diastolic function of the ventricle is even more sensitive to ischaemia than the systolic function. Tau is significantly lower in the group treated with Compound 1, compared to the control group 70 and 100 minutes after the end of the study period of ischaemia and also significantly lower in the ischaemic preconditioning group compared to the control group after 100 minutes of reperfusion (FIG. 4).

The parameter SW/PVA is a measure of the efficacy with which the cardiac mechanical work is used. Stroke work is the external mechanical work and PVA is the mechanical energy produced by the heart as the stroke work but also as the potential energy required to achieve pressure increase at a specific volume. So far, this PVA (pressure-volume-area) is the mechanical parameter with the best correlation to oxygen consumption. The greater the ratio SW/PVA, the more the ventricular work is used as external work to pump out the blood. The control group has a significantly lower SW/PVA ratio compared to both the ischaemic preconditioning group and the group treated with Compound 140, 70 and 100 minutes after the end of the study period of ischaemia (FIG. 5).

The contractile efficacy, which is a measure of the efficacy with which $O_2$-consumption is converted into PVA, or mechanical energy, is significantly greater in the ischaemic preconditioning group (44.5%) and group treated with Compound 1 (46.7%) compared to the control group (32.8%, p<0.001).

As a further advantage of the compounds according to the invention should be mentioned that the heart feels softer in the group treated with Compound 1 as compared to both the control group and the ischaemic preconditioning group.

In summary, the compounds according to the invention are at least as effective as conventional ischaemic preconditioning as a cardioprotective mechanism for 30 minutes' normothermic myocardial ischaemia during extra corporal circulation. It enhances contractility and cardiac diastolic function. Cardiac energetic efficacy, both $O_2$-consumption for the development of PVA and PVA conversion into external work SW, is also greater. The pharmacological protection with the compounds according to the invention is preferable over ischaemic preconditioning since they offer the same efficacy as ischaemic preconditioning, involves fewer risks (aorta cross-clamping, mild stunning) and is less time-consuming. Also, compared to the concentrations of DADLE used in similar experiments, the compounds according to the invention are administered in concentrations at least a factor of 10 lower.

D. CLINICAL EXPERIMENTS: CEREBRAL ISCHAEMIA

The reduction of cerebral ischaemia or the cerebroprotective action of the compounds according to the invention could be determined using a model of temporary forebrain ischaemia in the rat in which the infarction size is determined after occlusion of the middle cerebral artery (MCA), e.g. by suture. Such model is described in WO 96/27380. Also, to assess functional outcome after ischaemia, a number of behaviour tests could be performed as disclosed in WO 96/27380.

The invention claimed is:

1. A method for reducing damage to an organ in a mammal comprising administering to said mammal, prior to a surgical or percutaneous intervention procedure that includes an ischaemia-reperfusion sequence, a compound of Formula (I):

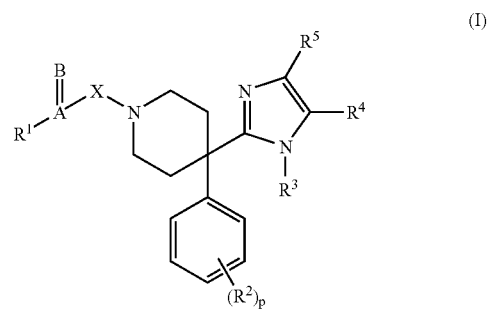

a pharmaceutically acceptable acid or base addition salt thereof, a stereochemically isomeric form thereof, a tautomeric form thereof or a N-oxide form thereof, wherein:

A=B is a bivalent -bond radical;

X is a covalent bond, —$CH_2$— or $CH_2CH_2$—;

$R^1$ is hydrogen, alkyloxy, alkylcarbonyloxy, Ar-oxy, Het-oxy, Ar-carbonyloxy, Het-carbonyloxy, Ar-alkyloxy, Het-alkyloxy, alkyl, polyhaloalkyl, alkyloxyalkyl, Ar-alkyl, Het-alkyl, Ar, Het, thio, alkylthio, Ar-thio, Het-thio or $NR^9R^{10}$ wherein $R^9$ and $R^{10}$ each independently are hydrogen, alkyl, Ar, Ar-alkyl, Het, Het-alkyl, alkyl-carbonyl, Ar-carbonyl, Het-carbonyl or alkyloxycarbonylalkyl;

or A=B and $R^1$ together form an optionally substituted semi-aromatic or aromatic carbocyclic or heterocyclic radical $Het^2$ or $Het^3$;

$R^2$ is hydroxy, alkyloxy, alkylcarbonyloxy, phenyloxy, phenylcarbonyloxy, halo, cyano, alkyl, polyhaloalkyl, alkyloxyalkyl, formyl, carboxy, alkylcarbonyl, alkyloxycarbonyl, aminocarbonyl, mono- or dialkylaminocarbonyl, phenyl, nitro, amino, mono- or dialkyl-amino, thio or alkylthio;

$R^3$ is alkyl, Ar, Ar-alkyl, Ar-alkenyl, Het, Het-alkyl or Het-alkenyl;

$R^4$, $R^5$ each independently is hydrogen, alkyl, carboxy, aminocarbonyl, alkyloxycarbonyl, halo or hydroxyalkyl;

p is an integer equal to zero, 1, 2 or 3;

alkyl is a straight or branched saturated hydrocarbon radical having from 1 to 6 carbon atoms; or is a cyclic saturated hydrocarbon (cycloalkyl) radical having from 3 to 7 carbon atoms; or is a cyclic saturated hydrocarbon radical having from 3 to 7 carbon atoms attached to a straight or branched saturated hydrocarbon radical having from 1 to 6 carbon atoms; wherein each carbon atom may be optionally substituted with amino, nitro, thio, hydroxy, oxo, cyano, formyl or carboxy;

alkenyl is an alkyl radical having one or more double bonds;

Ar is a homocycle selected from the group of phenyl and naphthyl, each optionally substituted with one or more substituents, each substituent independently selected from the group of hydroxy, alkyloxy, phenyloxy, phenylcarbonyloxy, polyhaloalkyloxy, halo, cyano, alkyl, polyhaloalkyl, alkyloxyalkyl, formyl, haloformyl, carboxy, alkylcarbonyl, alkyloxycarbonyl, aminocarbonyl, mono- or dialkylaminocarbonyl, phenylalkyl, phenyl, nitro, amino, mono- or dialkylamino, thio, alkylthio or $SO_2$—$CH_3$;

halo is a substituent selected from the group of fluoro, chloro, bromo and iodo;

polyhaloalkyl is a straight or branched saturated hydrocarbon radical having from 1 to 6 carbon atoms or a cyclic saturated hydrocarbon radical having from 3 to 7 carbon atoms, wherein one or more carbonatoms is substituted with one or more halo-atoms;

Het is a heterocyclic radical selected from the group of $Het^1$, $Het^2$ and $Het^3$, $Het^1$ is an aliphatic monocyclic heterocyclic radical selected from the group of pyrrolidinyl, dioxolyl, imidazolidinyl, pyrrazolidinyl, piperidinyl, dioxyl, morpholinyl, dithianyl, thiomorpholinyl, piperazinyl and tetrahydrofuranyl;

$Het^2$ is a semi-aromatic monocyclic heterocyclic radical selected from the group of 2H-pyrrolyl, pyrrolinyl, imidazolinyl and pyrrazolinyl;

$Het^3$ is an aromatic monocyclic heterocyclic radical selected from the group of pyrrolyl, pyrazolyl, imidazolyl, furanyl, thienyl, oxazolyl, isoxazolyl, thiazolyl, isothiazolyl, pyridinyl, pyrimidinyl, pyrazinyl, pyridazinyl and triazinyl; or an aromatic bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocyclic radical may optionally be substituted on a carbon and/or an heteroatom with halo, hydroxy, alkyloxy, alkyl, Ar, Ar-alkyl or pyridinyl.

2. The method according to claim 1, wherein the organ is a heart, a brain, a liver, a lung or a kidney.

3. The method according to claim 1, wherein the mammal is a human.

4. A method for inducing a protective effect in an organ in a mammal comprising administering to said mammal, prior to a surgical or percutaneous intervention procedure, wherein the surgical or percutaneous intervention procedure is transplant surgery, aneurysm surgery, vascular surgery for obstructive vascular disease, or percutaneous intervention on stenosed coronary, carotic, or peripheral arteries, a compound of Formula (I):

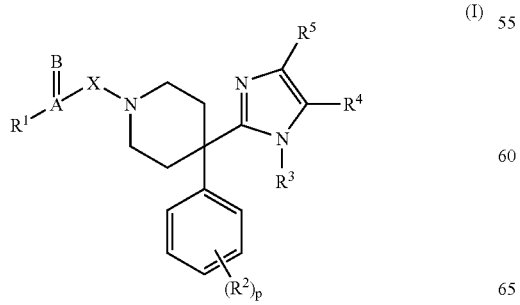

(I)

a pharmaceutically acceptable acid or base addition salt thereof, a stereochemically isomeric form thereof, a tautomeric form thereof or a N-oxide form thereof, wherein:

A=B is a bivalent -bond radical;

X is a covalent bond; —$CH_2$— or $CH_2CH_2$—;

$R^1$ is hydrogen, alkyloxy, alkylcarbonyloxy, Ar-oxy, Het-oxy, Ar-carbonyloxy, Het-carbonyloxy, Ar-alkyloxy, Het-alkyloxy, alkyl, polyhaloalkyl, alkyloxyalkyl, Ar-alkyl, Het-alkyl, Ar, Het, thio, alkylthio, Ar-thio, Het-thio or $NR^9R^{10}$ wherein $R^9$ and $R^{10}$ each independently are hydrogen, alkyl, Ar, Ar-alkyl, Het, Het-alkyl, alkyl-carbonyl, Ar-carbonyl, Het-carbonyl or alkyloxycarbonylalkyl;

or A=B and $R^1$ together form an optionally substituted semi-aromatic or aromatic carbocyclic or heterocyclic radical $Het^2$ or $Het^3$;

$R^2$ is hydroxy, alkyloxy, alkylcarbonyloxy, phenyloxy, phenylcarbonyloxy, halo, cyano, alkyl, polyhaloalkyl, alkyloxyalkyl, formyl, carboxy, alkylcarbonyl, alkyloxycarbonyl, aminocarbonyl, mono- or dialkylaminocarbonyl, phenyl, nitro, amino, mono- or dialkyl-amino, thio or alkylthio;

$R^3$ is alkyl, Ar, Ar-alkyl, Ar-alkenyl, Het, Het-alkyl or Het-alkenyl;

$R^4$, $R^5$ each independently is hydrogen, alkyl, carboxy, aminocarbonyl, alkyloxycarbonyl, halo or hydroxyalkyl;

p is an integer equal to zero, 1, 2 or 3;

alkyl is a straight or branched saturated hydrocarbon radical having from 1 to 6 carbon atoms; or is a cyclic saturated hydrocarbon (cycloalkyl) radical having from 3 to 7 carbon atoms; or is a cyclic saturated hydrocarbon radical having from 3 to 7 carbon atoms attached to a straight or branched saturated hydrocarbon radical having from 1 to 6 carbon atoms; wherein each carbon atom may be optionally substituted with amino, nitro, thio, hydroxy, oxo, cyano, formyl or carboxy;

alkenyl is an alkyl radical having one or more double bonds;

Ar is a homocycle selected from the group of phenyl and naphthyl, each optionally substituted with one or more substituents, each substituent independently selected from the group of hydroxy, alkyloxy, phenyloxy, phenylcarbonyloxy, polyhaloalkyloxy, halo, cyano, alkyl, polyhaloalkyl, alkyloxyalkyl, formyl, haloformyl, carboxy, alkylcarbonyl, alkyloxycarbonyl, aminocarbonyl, mono- or dialkylaminocarbonyl, phenylalkyl, phenyl, nitro, amino, mono- or dialkylamino, thio, alkylthio or $SO_2$—$CH_3$;

halo is a substituent selected from the group of fluoro, chloro, bromo and iodo;

polyhaloalkyl is a straight or branched saturated hydrocarbon radical having from 1 to 6 carbon atoms or a cyclic saturated hydrocarbon radical having from 3 to 7carbon atoms, wherein one or more carbonatoms is substituted with one or more halo-atoms;

Het is a heterocyclic radical selected from the group of $Het^1$, $Het^2$ and $Het^3$.

$Het^1$ is an aliphatic monocyclic heterocyclic radical selected from the group of pyrrolidinyl, dioxolyl, imidazolidinyl, pyrrazolidinyl, piperidinyl, dioxyl, morpholinyl, dithianyl, thiomorpholinyl, piperazinyl and tetrahydrofuranyl;

Het² is a semi-aromatic monocyclic heterocyclic radical selected from the group of 2H-pyrrolyl, pyrrolinyl, imidazolinyl and pyrrazolinyl;

Het³ is an aromatic monocyclic heterocycic radical selected from the group of pyrrolyl, pyrazolyl, imidazolyl, furanyl, thienyl, oxazolyl, isoxazolyl, thiazolyl, isothiazolyl, pyridinyl, pyrimidinyl, pyrazinyl, pyridazinyl and triazinyl; or an aromatic bicycic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocyclic radical may optionally be substituted on a carbon and/or an heteroatom with halo, hydroxy, alkyloxy, alkyl, Ar, Ar-alkyl or pyridinyl.

5. The method according to claim 4, wherein the organ is a heart, a brain, a liver, a lung or a kidney.

6. The method according to claim 4, wherein the mammal is a human.

7. The method according to claim 1 or claim 4, wherein A=B is C=O, C=2 N-R wherein $R^6$ is hydrogen or cyano, C=S, S=O, $SO_2$ or $C=CR^7R^8$ wherein $R^7$ and $R^8$ each independently are hydrogen, nitro or alkyl.

8. The method according to claim 1 or claim 4, wherein $R^1$ is alkyloxy, Ar-alkyloxy, alkyl, polyhaloalkyl, alkyloxyalkyl, Ar-alkyl, Het-alkyl, Ar, piperazinyl, pyrrolyl, thiazolyl, pyrrolidinyl or $NR^9R^{10}$ wherein $R^9$ and $R^{10}$ each independently are hydrogen, alkyl, Ar, Ar-alkyl, pyridinyl or alkyloxycarbonylalkyl.

9. The method according to claim 1 or claim 4, wherein A=B and $R^1$ together form a radical selected from the group of Het² and Het³.

10. The method according to claim 1 or claim 4, wherein A=B and $R^1$ together form a radical selected from the group of benzoxazolyl, thiazolyl, benzothiazolyl, benzimidazolyl and pyrimidinyl.

11. The method according to claim 1 or claim 4, wherein X is a covalent bond.

12. The method according to claim 1 or claim 4, wherein $R^2$ is alkyloxy or halo.

13. The method according to claim 1 or claim 4, wherein $R^3$ is phenylalkyl or napthyl, each independently substituted with at least one substituent selected from the group of halo, alkyloxycarbonyl, hydroxy, alkyloxy and dialkylaminocarbonyl.

14. The method according to claim 1 or claim 4, wherein A=B is C=O or $SO_2$, $R^1$ is alkyloxy, alkyloxyalkyl, Ar or $NR^9R^{10}$, wherein $R^9$ and $R^{10}$ each independently are hydrogen or Ar; or A=B and $R^1$ together form a benzoxazolyl radical; p is zero, $R^3$ is benzyl optionally substituted with hydroxy or alkyloxycarbonyl and $R^4$ and $R^5$ each are hydrogen.

15. The method according to claim 1 or claim 4, wherein the compound is:
  1-ethoxycarbonyl-4-phenyl-4-[1-(phenylmethyl)-1H-imidazol-2-yl]-piperidine;
  1-propyloxycarbonyl-4-phenyl4-[1-(phenylmethyl)-1H-imidazol-2-yl]-piperidine;
  1-ethoxycarbonyl-4-phenyl-4-[1-[(4-hydroxyphenyl)methyl]-1H-imidazol-2-yl]-piperidine;
  1-ethoxycarbonyl-4-phenyl-4-[1-(1-phenylethyl)-1H-imidazol-2-yl]-piperidine;
  1-isopropyloxycarbonyl-4-phenyl-4-[1-(phenylmethyl)-1H-imidazol-2-yl]-piperidine;
  1-ethoxycarbonyl-4-phenyl-4-[1-[[4-(methoxycarbonyl)phenyl]methyl]-1H-imidazol-2-yl]-piperidine;
  1-benzoyl-4-phenyl4-[1-(phenylmethyl)-1H-imidazol-2-yl]-piperidine;
  1-(methoxyacetyl)-4-phenyl-4-[1-(1-phenylethyl)-1H-imidazol-2-yl]-piperidine;
  4-[[2-(1-benzoyl-4-phenyl-4-piperidinyl)-1H-imidazol-1-yl]methyl]-methylbenzoate;
  4-[[2-[1-(2-benzoxazolyl)4-phenyl-4-piperidinyl]-1H-imidazol-1-yl]methyl]-methylbenzoate;
  1-benzoyl-4-phenyl-4-[1-(1-phenylethyl)-1H-imidazol-2-yl]-piperidine;
  1-ethoxycarbonyl-4-phenyl-4-[1-[1-[4-(ethoxycarbonyl)phenyl]ethyl]-1H-imidazol-2-yl]-piperidine; or
  N,4-diphenyl-4-[1-(phenylmethyl)-1H-imidazol-2-yl]-1-piperidinesulfonamide.

16. The method according to claim 1 or 4, wherein said surgical or percutaneous intervention procedure is characterized by reduced blood supply to said organ.

* * * * *